(12) United States Patent
Raguse et al.

(10) Patent No.: US 6,417,009 B1
(45) Date of Patent: Jul. 9, 2002

(54) RESERVOIR COMPONENTS

(75) Inventors: Burkhard Raguse, St. Ives; Christopher John Burns, Balmain; Leslie David Field, Riverview; Damon Donald Ridley, Chippendale, all of (AU)

(73) Assignees: Australian Membrane and Biotechnology Institute, New South Wales; The University of Sydney, Sydney, both of (AU)

( * ) Notice: Subject to any disclaimer, the term of this patent is extended or adjusted under 35 U.S.C. 154(b) by 0 days.

(21) Appl. No.: 09/180,489

(22) PCT Filed: May 13, 1997

(86) PCT No.: PCT/AU97/00294

§ 371 (c)(1),
(2), (4) Date: Mar. 8, 1999

(87) PCT Pub. No.: WO97/43274

PCT Pub. Date: Nov. 20, 1997

(30) Foreign Application Priority Data

May 13, 1996 (AU) ............................................ PN 9807

(51) Int. Cl.[7] .................... G01N 33/543; G01N 27/00; G01N 27/26; C12M 3/00; B05D 3/00
(52) U.S. Cl. .................. 436/518; 436/71; 436/528; 436/806; 435/287.1; 435/289.1; 435/291; 435/817; 422/82.01; 422/82.03; 427/2.11; 427/2.13; 427/58; 427/337; 427/338; 204/296; 204/418; 204/400; 204/403; 204/415; 204/416
(58) Field of Search ........................... 204/153.12, 403, 204/418, 153.1, 415, 416, 400, 296; 422/82.01, 82.03; 435/287.1, 817, 289.1, 291; 436/71, 518, 528, 806; 427/2.11, 2.13, 58, 337, 338

(56) References Cited

U.S. PATENT DOCUMENTS

| | | | | |
|---|---|---|---|---|
| 4,810,351 A | * | 3/1989 | Chapoteau et al. ......... 204/418 |
| 5,204,239 A | * | 4/1993 | Gitler et al. .................. 435/7.1 |
| 5,401,378 A | * | 3/1995 | King et al. .................. 204/418 |
| 5,443,955 A | * | 8/1995 | Cornell et al. .............. 435/7.21 |
| 5,766,960 A | * | 6/1998 | Cornell et al. .............. 436/501 |
| 5,783,054 A | * | 7/1998 | Raguse et al. .............. 204/296 |
| 5,798,030 A | * | 8/1998 | Raguse et al. .............. 204/403 |
| 5,834,224 A | * | 11/1998 | Ruger et al. .................. 435/14 |
| 5,840,083 A | * | 11/1998 | Braach-Maksvytis ........ 623/11 |
| 5,879,878 A | * | 3/1999 | Raguse et al. .................. 435/4 |
| 6,287,807 B1 | | 9/2001 | Wallis ....................... 435/69.1 |

FOREIGN PATENT DOCUMENTS

| | | |
|---|---|---|
| AU | B-50334/90 | 8/1990 |
| AU | 14657/92 | 11/1992 |
| AU | 51444/93 | 4/1994 |
| WO | WO 89/01159 | 2/1989 |
| WO | WO 90/02327 | 3/1990 |
| WO | WO 92/17788 | 10/1992 |
| WO | WO 94/07593 | 4/1994 |
| WO | WO 94/24562 | 10/1994 |
| WO | 95/21528 | 8/1995 |
| WO | WO A 96/12957 | 5/1996 |
| WO | WO 96/15454 | 5/1996 |
| WO | WO 96/36871 | 11/1996 |
| WO | WO-97/01092 A1 * | 1/1997 |

* cited by examiner

Primary Examiner—Christopher L. Chin
Assistant Examiner—Kartic Padmanabhan
(74) Attorney, Agent, or Firm—Nixon & Vanderhye

(57) ABSTRACT

A linker lipid for use in attaching a membrane including a plurality of ionophores to an electrode and providing a space between the membrane and the electrode in which the membrane is either in part or totally made up of the linker lipid. The linker lipid has within the same molecule a hydrophobic region capable of spanning the membrane, an attachment group used to attach the molecule to an electrode surface, a hydrophilic region intermediate the hydrophobic region and the attachment group, and a polar head group region attached to the hydrophobic region at a site remote from the hydrophilic region. The attachment group has a cross sectional area greater than the cross sectional area of the hydrophilic region, and has the structure recited in the specification.

39 Claims, 3 Drawing Sheets

Figure 2: Linker lipid A
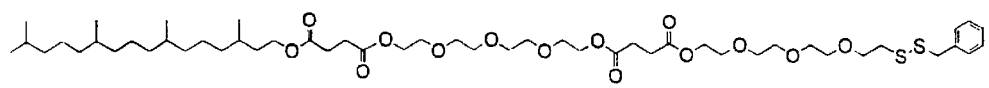
Figure 3: Linker gramicidin B
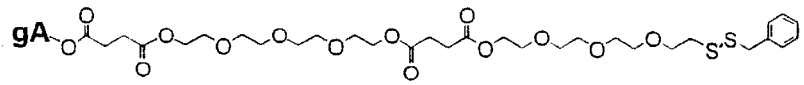
where gA is
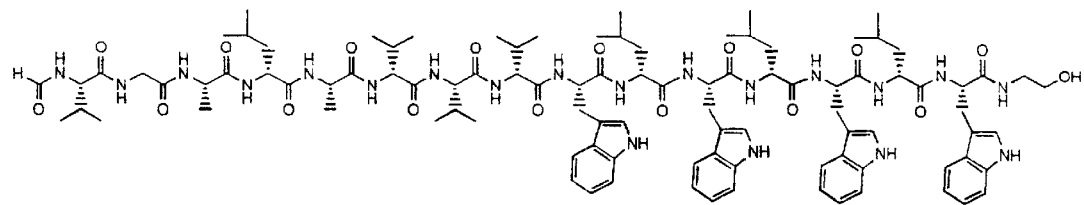

Figure 4: Membrane spanning lipid
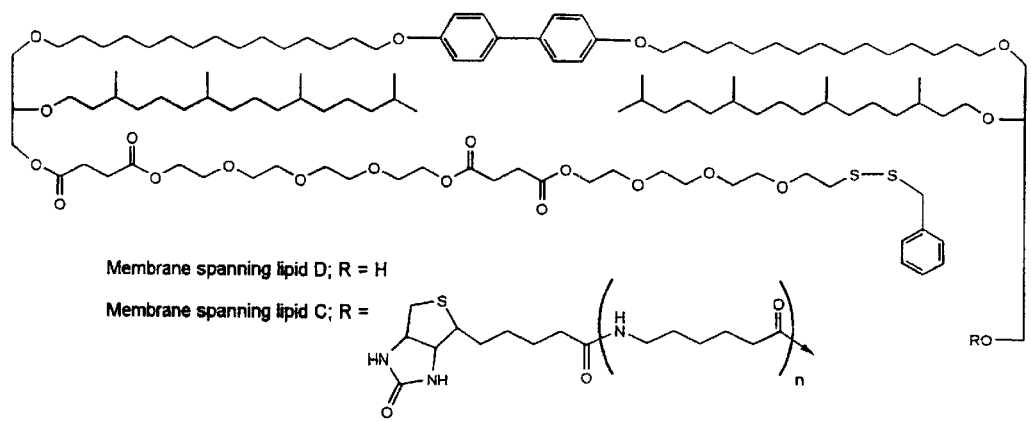
Figure 5: Biotinylated gramicidin E
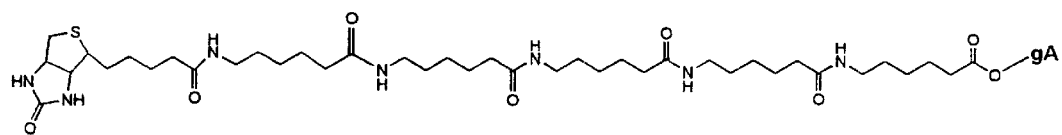
where gA is as shown in Figure 3.

RESERVOIR COMPONENTS

This application is a 371 of PCT International Application No. PCT/AU97/00294, filed May 13, 1997.

FIELD OF THE INVENTION

The present invention relates to novel molecules which may be advantageously incorporated in membrane based biosensors.

BACKGROUND OF THE INVENTION

Previous patents such as WO 92/17788, U.S. Pat. No. 5,204,239 and WO 93/21528 (the disclosures of which are incorporated herein by reference) have described how functional biosensor bilayer or monolayer lipid membranes may be formed on a metal substrate such that a functioning ionic reservoir is formed between the metal surface and the lipid membrane. The inner leaflet of the membrane, or in the case of the monolayer membrane the whole membrane is typically assembled using molecules that comprise within the same molecule a hydrophobic group linked to a hydrophilic group onto which is attached an attachment group such as a disulfide or thiol group capable of attaching the molecule to an electrode. Furthermore, it has been disclosed in WO 94/07593 (the disclosure of which is also included herein by reference) that in order to provide improved reservoir characteristics and fluidity characteristics of the membrane a small spacer molecule, such as the disulfide of mercaptoacetic acid, should be incorporated between the reservoir molecules that had been adsorbed onto the metal surface.

The present inventors have now determined that if the functionality of the small spacer molecule is covalently incorporated into the reservoir molecules described previously, such that a single molecule is formed, then improvements in stability and reproducibility of the membrane formation, as well as improved ionophore conduction can be achieved. Additionally the manufacture of the membrane is simplified as fewer components are required.

SUMMARY OF THE INVENTION

Accordingly, in a first aspect, the present invention consists in a linker lipid for use in attaching a membrane including a plurality of ionophores to an electrode and providing a space between the membrane and the electrode in which the membrane is either in part or totally made up of the linker lipid, the linker lipid comprising within the same molecule a hydrophobic region capable of spanning the membrane, an attachment group used to attach the molecule to an electrode surface, a hydrophilic region intermediate said hydrophobic region and the attachment group, and a polar head group region attached to the hydrophobic region at a site remote from the hydrophilic region wherein said attachment group has a cross sectional area that is at least two times the cross sectional area of the hydrophilic region.

It is preferred that the head group, hydrophobic region, and hydrophilic region are as described previously in WO 92/17788 and WO 94/07593. The linker lipid in this case may be wholly synthetic or derived from naturally occurring membrane spanning lipids or archaebacterial lipids.

The hydrophilic region of the linker lipid is preferably a long chain hydrophilic compound. The hydrophilic region of the linker lipid may be composed of oligo/poly ethers, oligo/poly peptides, oligo/poly amides, oligo/poly amines, oligo/poly esters, oligo/poly saccharides, polyols, multiple charged groups (positive and/or negative), electroactive species or combinations thereof. The main requirement of the hydrophilic region of the linker lipid is that it allows the diffusion of ions through the ionophores provided in the membrane. This is achieved by the placement of suitable ion and/or water binding sites along or within the length of the long chain that makes up the reservoir region.

In a preferred embodiment of the invention the hydrophilic region consists of an oligoethylene oxide group. The oligoethylene oxide group may consist of four to twenty ethylene oxide units.

In a further preferred embodiment the hydrophilic region consists of a subunit of tetraethylene glycol attached to succinic acid. This tetraethylene glycol/succinic acid subunit may be repeated 1–4 times.

In a further preferred embodiment the hydrophilic region is formed by group transfer or anionic polymerisation of suitable monomers.

In a further preferred embodiment the hydrophilic region consists of mercaptoethanol, succinic acid, 1,4-diesterified 1,2,3,4-butanetetraol and succinic acid subunits. The succinic acid/1,4-diesterified 1,2,3,4-butanetetraol may be repeated 1–4 times.

In yet another embodiment the hydrophilic region may consist of an oligopropylene glycol of between 1 to 20 propylene glycol units in length. It is further preferred that the hydrophilic region consists oligopropylene glycols of between 2 and 8 propylene glycol units that are functionalised at each end with an N-alkyl amine functionality and that may be joined together via acid units forming tertiary amides.

It is further preferred that the hydrophilic region consists of oligoethylene glycols of between 2 and 10 ethylene glycol units that are functionalised at each end with an N-alkyl amine functionality and that may be joined together via acid units forming tertiary amides.

In a preferred embodiment of the present invention the head group of the linker lipid comprises a receptor reactive with an analyte or a group capable of attaching to a protein receptor.

In a preferred embodiment, the head group comprises a biotin or biotin derivative capable of complexing streptavidin, avidin or one of the common biotin binding proteins.

In a further preferred embodiment the biotin group is linked to the linker lipid via 1 to 8 aminocaproyl groups.

In a further preferred embodiment two biotin groups are attached to the linker lipid such that both biotin groups are capable of complexing a single avidin or streptavidin molecule so as to increase the overall complexing ability and strength of the linker lipid to the avidin or streptavidin.

In a further preferred embodiment of the present invention the hydrophobic region of the membrane spanning lipid comprises a hydrocarbon backbone of between 20–60 angstroms in length with sites of attachment at either end of the hydrocarbon backbone to which are attached at least two hydrocarbon side chains such as phytanyl chains.

In a further preferred embodiment of the present invention the hydrophobic region of the membrane spanning lipid comprises a hydrocarbon backbone of between 20–60 angstroms in length with sites of attachment at either end of the hydrocarbon backbone to which are attached at one end zero or one hydrocarbon sidechain and at least two to four hydrocarbon sidechains at the other end.

The hydrocarbon backbone may comprise a straight methylene chain hydrocarbon, or a hydrocarbon chain optionally substituted with additional groups selected from alkyl, aryl, ether and amine groups, or may comprise two shorter hydrocarbon chains that have been joined via ether, amine, or biphenyl ether groups. Those skilled in the art will appreciate that other functionalities that can link two hydrocarbon chains may also be employed.

It is preferred that the means by which the hydrocarbon chains are attached to the hydrocarbon backbone is via a polyhydroxylated hydrocarbon containing from 3 to 20 hydroxyl groups.

It is further preferred that the means by which the hydrocarbon sidechains are attached to the hydrocarbon backbone is via glycerol, glutamic acid, erythritol, threitol or pentaerythritol groups.

It is preferred that the length of the hydrocarbon sidechains are approximately half the total length of the hydrocarbon backbone.

It is further preferred that the hydrocarbon sidechains are phytanyl chains.

It is further preferred that the hydrocarbon sidechains are mono- or per-methylated hydrocarbon chains or a hydrocarbon chain optionally substituted with additional groups selected from alkyl, aryl, ether and amine groups.

It is preferred that for the case of the electrode material being a gold, platinum, palladium, silver or other coinage metal substrate or combination thereof, the attachment region includes sulfur containing groups such as thiols, disulfides, sulfides thiocyanates. However as previously described, other groups such as organosilanes that form strong attachment to a variety of conductive substrates may also be used.

In the case where the hydrophilic region of the linker lipid is a single chain it is preferred that the attachment region of the molecule is an array containing two to twenty sulfur atoms.

It is further preferred that the attachment region includes between one to three disulfide groups.

Further preferred that the attachment region includes up to 6 thiol groups.

It is further preferred that the attachment group has the following structure:

where X is either a carbon, nitrogen or oxygen to which the hydrophilic region is attached, Y is a carbon or if X is a carbon Y may be a nitrogen, n is between 1 to 6, m is between 1 to 3 if Y is a carbon and between 1 to 2 if Y is a nitrogen, and R is a small group such as any of the following —SH, —SCH$_2$Ph, —SCH$_2$CO$_2$H, —SCH$_2$CH$_2$CO$_2$H, —SCH$_2$CH$_2$OH, —SCH$_2$CH$_2$CH$_2$OH, —SCH$_3$, —SCH$_2$CH$_3$, —SCH$_2$CH$_2$CH$_3$, —SCH2CO$_2$CH$_3$, —SCH$_2$CO$_2$CH$_2$CH$_3$, an a containing between 1 and 4 carbon atoms, or an aryl group.

In a further preferred embodiment of the present invention the attachment group has the following structure:

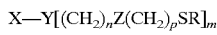

where X is either a carbon, nitrogen or oxygen to which the hydrophilic region is attached, Y is a carbon or if X is a carbon Y may be a nitrogen, m is between 1 to 3 if Y is a carbon and between 1 to 2 if Y is a nitrogen, where Z is O, NH, NR$^1$, an amide or ketone, and where n is between 1 and 5 and p is between 2 and 5, unless Y is N, in which case n is between 2 and 5, and where R$^1$ is an alkyl chain containing between 1 and 4 carbon atoms, and R is a small group such as any of the following —SH, —SCH$_2$Ph, —SCH$_2$CO$_2$H, —SCH$_2$CH$_2$CO$_2$H, —SCH$_2$CH$_2$OH, —SCH$_2$CH$_2$CH$_2$OH, —SCH$_3$, —SCH$_2$CH$_3$, —SCH$_2$CH$_2$CH$_3$, —SCH2CO$_2$CH$_3$, —SCH$_2$CO$_2$CH$_2$CH$_3$, an alkyl chain containing between 1 and 4 carbon atoms, or an aryl group.

It is further prefered that the attachment group is thiooctic acid or bis-thiooctic acid derivative.

It is further preferred that the attachment group is the cyclic oxidised form of dithiothreitol.

It is further preferred that the attachment group contains one to three bis(4-hydroxymethyl)-1,2-dithiacyclopentane groups.

It is further preferred that the attachment group contains a bis(4-hydroxymethyl)-1,2-dithiacyclopentane groups where the hydrophilic reservoir is attached via one of the 4-hydroxymethyl moieties of the bis(4-hydroxymethyl)-1,2-dithiacyclopentane and where the other 4-hydroxymethyl moiety may be the hydroxy functionality or may have been further functionalised to a methyl ether, ethyl ether, propyl ether, acetate, or succinate, or a group of the formula (CH$_2$)$_n$COZ where n is 0 to 4, and Z is OR, or NR$^1$R$^2$, where R, R$^1$ and R$^2$ are independently hydrogen or alkyl chains containing between 1 and 4 carbon atoms.

It is further preferred that the attachment group contains a bis(4-hydroxymethyl)-1,2-dithiacyclopentane groups where the hydrophilic reservoir is attached via one of the 4-hydroxymethyl moieties of the bis(4-hydroxymethyl)-1,2-dithiacyclopentane and where the other 4-hydroxymethyl moiety may be linked to between one and three other bis(4-hydroxymethyl)-1,2-dithiacyclopentane groups.

It is further preferred that the linking group be ethyleneoxy or diethyleneoxy.

It is further preferred that the attachment group contains one to three dithiothreitol groups.

It is further preferred that the attachment group contains a trans-4,5-dihydroxy-1,2-dithiacyclohexane groups where the hydrophilic reservoir is attached via one of the 4,5-hydroxy moieties of the trans-4,5-dihydroxy-1,2-dithiacyclohexane and where the other 4,5-hydroxy moiety may be the hydroxy functionality or may have been further functionalised to a methyl ether, ethyl ether, propyl ether, acetate, or succinate, or a group of the formula (CH$_2$)$_n$COZ where n is 0 to 4, and Z is OR, or NR$^1$R$^2$, where R, R$^1$ and R$^2$ are independently hydrogen or alkyl chains containing between 1 and 4 carbon atoms.

It is further preferred that the attachment group contains a trans-4,5-dihydroxy-1,2-dithiacyclohexane groups where the hydrophilic reservoir is attached via one of the 4,5-hydroxy moieties of the trans-4,5-dihydroxy-1,2-dithiacyclohexane and where the other 4,5-hydroxy moiety may be linked to between one and three other trans-4,5-dihydroxy-1,2-dithiacyclohexane groups.

In a further preferred embodiment the cross sectional area of the hydrophobic region is similar to the cross sectional area of the attachment group as shown schematically in FIG. 1.

In a second aspect, the present invention consists in a linker lipid for use in attaching a bilayer membrane including a plurality of ionophores to an electrode and providing a space between the membrane and the electrode in which the membrane layer proximate the electrode is either in part or totally made up of the linker lipid, the linker lipid comprising within the same molecule a hydrophobic region which spans half the membrane, an attachment group used to attach the molecule to an electrode surface, and a hydrophilic region intermediate said hydrophobic region and the attachment group, wherein said attachment group has a cross sectional area that is at least two times the cross sectional area of the hydrophilic region.

It is preferred that the hydrophobic region is a phytanyl chain.

It is further preferred that the hydrophobic region is a mono- or per-methylated hydrocarbon chain or a hydrocarbon chain optionally substituted with additional groups selected from alkyl, aryl, ether and amine groups.

It is preferred that the hydrophobic region is comprised of a polyether containing hydrocarbon chains, such as phytanyl, attached to polyol.

It is further preferred that the hydrophobic region comprises 2 to 4 hydrocarbon chains such as phytanyl chains.

It is further preferred that the hydrophobic region comprise a diphytanyl glyceryl ether.

It is further preferred that the hydrophobic region comprise a triphytanyl pentaerythrityl ether.

It is further preferred that the hydrophobic region comprise a triphytanyl threityl ether.

It is further preferred that the hydrophobic region comprise a triphytanyl erythritol ether.

It is preferred that for the case of the electrode material being a gold, platinum, palladium, silver or other coinage metal substrate or combination thereof, the attachment region includes sulfur containing groups such as thiols, disulfides, sulfides thiocyanates. However as previously described, other groups such as organosilanes that form strong attachment to a variety of conductive substrates may also be used.

In the case where the hydrophilic region of the linker lipid is a single chain it is preferred that the attachment region of the molecule is an array containing two to twenty sulfur atoms.

It is further preferred that the attachment region includes between one to three disulfide groups.

Further preferred that the attachment region includes up to 6 thiol groups.

It is further preferred that the attachment group has the following structure:

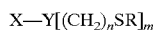

where X is either a carbon, nitrogen or oxygen to which the hydrophilic region is attached, Y is a carbon or if X is a carbon Y may be a nitrogen, n is between 1 to 6, m is between 1 to 3 if Y is a carbon and between 1 to 2 if Y is a nitrogen, and R is a small group such as any of the following —SH, —SCH$_2$Ph, —SCH$_2$CO$_2$H, —SCH$_2$CH$_2$CO$_2$H, —SCH$_2$CH$_2$OH, —SCH$_2$CH$_2$CH$_2$OH, —SCH$_3$, —SCH$_2$CH$_3$, —SCH$_2$CH$_2$CH$_3$, —SCH2CO$_2$CH$_3$, —SCH$_2$CO$_2$CH$_2$CH$_3$, an alkyl chain containing between 1 and 4 carbon atoms, or an aryl group.

In a further preferred embodiment of the present invention the attachment group has the following structure:

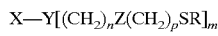

where X is either a carbon, nitrogen or oxygen to which the hydrophilic region is attached, Y is a carbon or if X is a carbon Y may be a nitrogen, m is between 1 to 3 if Y is a carbon and between 1 to 2 if Y is a nitrogen, where Z is O, NH, NR$^1$, an amide or ketone, and where n is between 1 and 5 and p is between 2 and 5, unless Y is N, in which case n is between 2 and 5, and where R$^1$ is an alkyl chain containing between 1 and 4 carbon atoms, and R is a small group such as any of the following —SH, —SCH$_2$Ph, —SCH$_2$CO$_2$H, —SCH$_2$CH$_2$CO$_2$H, —SCH$_2$CH$_2$OH, —SCH$_2$CH$_2$CH$_2$OH, —SCH$_3$, —SCH$_2$CH$_3$, —SCH$_2$CH$_2$CH$_3$, —SCH2CO$_2$CH$_3$, —SCH$_2$CO$_2$CH$_2$CH$_3$, an alkyl chain containing between 1 and 4 carbon atoms, or an aryl group.

It is further prefered that the attachment group is thiooctic acid or bis-thiooctic acid derivative.

It is further preferred that the attachment group is the cyclic oxidised form of dithiothreitol.

It is further preferred that the attachment group contains one to three bis(4-hydroxymethyl)-1,2-dithiacyclopentane groups.

It is further preferred that the attachment group contains a bis(4-hydroxymethyl)-1,2-dithiacyclopentane groups where the hydrophilic region is attached via one of the 4-hydroxymethyl moieties of the bis(4-hydroxymethyl)-1,2-dithiacyclopentane and where the other 4-hydroxymethyl moiety may be the hydroxy functionality or may have been further functionalised to a methyl ether, ethyl ether, propyl ether, acetate, or succinate. or a group of the formula (CH$_2$)$_n$COZ where n is 0 to 4, and Z is OR, or NR$^1$R$^2$, where R, R$^1$ and R$^2$ are independently hydrogen or alkyl chains containing between 1 and 4 carbon atoms.

It is further preferred that the attachment group contains a bis(4-hydroxymethyl)-1,2-dithiacyclopentane groups where the hydrophilic region is attached via one of the 4-hydroxymethyl moieties of the bis(4-hydroxymethyl)-1,2-dithiacyclopentane and where the other 4-hydroxymethyl moiety may be linked to between one and three other bis(4-hydroxymethyl)-1,2-dithiacyclopentane groups.

It is further preferred that the linking group be ethyleneoxy or diethyleneoxy.

It is further preferred that the attachment group contains one to three dithiothreitol groups.

It is further preferred that the attachment group contains a trans-4,5-dihydroxy-1,2-dithiacyclohexane groups where the hydrophilic region is attached via one of the 4,5-hydroxy moieties of the trans-4,5-dihydroxy-1,2-dithiacyclohexane and where the other 4,5-hydroxy moiety may be the hydroxy functionality or may have been further functionalised to a methyl ether, ethyl ether, propyl ether, acetate, or succinate, or a group of the formula (CH$_2$)$_n$COZ where n is 0 to 4, and Z is OR, or NR$^1$R$^2$, where R, R$^1$ and R$^2$ are independently hydrogen or alkyl chains containing between 1 and 4 carbon atoms.

It is further preferred that the attachment group contains a trans-4,5-dihydroxy-1,2-dithiacyclohexane groups where the hydrophilic region is attached via one of the 4,5-hydroxy moieties of the trans-4,5-dihydroxy-1,2-dithiacyclohexane and where the other 4,5-hydroxy moiety may be linked to between one and three other trans-4,5-dihydroxy-1,2-dithiacyclohexane groups.

Ionophore ion channels such as gramicidin generally need to assume a particular conformation in order to form conducting channels. Gramicidin A for instance is thought to assume a beta-helical structure in its conducting form. It is thought that if there is sufficient crowding of the linker gramicidin by linker lipid molecules during the deposition of the inner sulfur/gold lipid layer, then this crowding may adversely affect the ability of the ion channel to assume its proper conformation and hence reduce its capability of forming conducting channels. Previously this crowding was thought to be minimised by the use of small sulfur containing spacer molecules. A more controllable method is to increase the cross sectional area of the attachment group such that its cross sectional area is comparable to the cross sectional area of the ion channel.

Hence, in a third aspect, the present invention consists in a linker ion channel for use in a bilayer or monolayer membrane based biosensor including an electrode, said linker ion channel comprising within the same molecule a hydrophobic ion channel which spans at least half the membrane, an attachment group to attach the linker ion channel to the electrode surface, a hydrophilic region intermediate said hydrophobic ion channel and the attachment group, wherein said attachment group has a cross sectional area that is at least the cross sectional area of the hydrophobic ion channel.

It is preferred that the ion channel is gramicidin or one of its derivatives.

It is further preferred that the ion channel is a synthetic ion channel.

It is preferred that for the case of the electrode material being a gold, platinum, palladium, silver or other coinage metal substrate or combination thereof, the attachment region includes sulfur containing groups such as thiols, disulfides, sulfides thiocyanates. However as previously described, other groups such as organosilanes that form strong attachment to a variety of conductive substrates may also be used.

In the case where the hydrophilic region of the linker lipid is a single chain it is preferred that the attachment region of the molecule is an array containing two to twenty sulfur atoms.

It is further preferred that the attachment region includes between one to three disulfide groups.

Further preferred that the attachment region includes up to 6 thiol groups.

It is further preferred that the attachment group has the following structure:

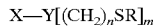
X—Y[(CH$_2$)$_n$SR]$_m$ where X is either a carbon, nitrogen or oxygen to which the hydrophilic region is attached, Y is a carbon or if X is a carbon Y may be a nitrogen, n is between 1 to 6, m is between 1 to 3 if Y is a carbon and between 1 to 2 if Y is a nitrogen, and R is a small group such as any of the following —SH, —SCH$_2$Ph, —SCH$_2$CO$_2$H, —SCH$_2$CH$_2$CO$_2$H, —SCH$_2$CH$_2$OH, —SCH$_2$CH$_2$CH$_2$OH, —SCH$_3$, —SCH$_2$CH$_3$, —SCH$_2$CH$_2$CH$_3$, —SCH2CO$_2$CH$_3$, —SCH$_2$CO$_2$CH$_2$CH$_3$, an alkyl chain containing between 1 and 4 carbon atoms, or an aryl group.

In a further preferred embodiment of the present invention the attachment group has the following structure:

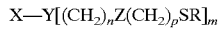
X—Y[(CH$_2$)$_n$Z(CH$_2$)$_p$SR]$_m$ where X is either a carbon, nitrogen or oxygen to which the hydrophilic region is attached, Y is a carbon or if X is a carbon Y may be a nitrogen, m is between 1 to 3 if Y is a carbon and between 1 to 2 if Y is a nitrogen, where Z is O, NH, NR$^1$, an amide or ketone, and where n is between 1 and 5 and p is between 2 and 5, unless Y is N, in which case n is between 2 and 5, and where R$^1$is. an alkyl chain containing between 1 and 4 carbon atoms, and R is a small group such as any of the following —SH, —SCH$_2$Ph, —SCH$_2$CO$_2$H, —SCH$_2$CH$_2$CO$_2$H, —SCH$_2$CH$_2$OH, —SCH$_2$CH$_2$CH$_2$OH, —SCH$_3$, —SCH$_2$CH$_3$, —SCH$_2$CH$_2$CH$_3$, —SCH2CO$_2$CH$_3$, —SCH$_2$CO$_2$CH$_2$CH$_3$, an alkyl chain containing between 1 and 4 carbon atoms, or an aryl group.

In a further preferred embodiment of the present invention the attachment group has the following structure:

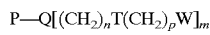
P—Q[(CH$_2$)$_n$T(CH$_2$)$_p$W]$_m$ where P either a carbon, nitrogen or oxygen to which the hydrophilic reservoir region is attached, Q is a carbon or if P is a carbon Q may be a nitrogen, n is between 1 to 6, m is between 1 to 3 if Q is a carbon and between 1 to 2 if Q is a nitrogen, T is O, NH, NR$^1$, an amide or ketone, and where n is between 1 and 5 and p is between 2 and 5, unless Q is N, in which case n is between 2 and 5, and where R$^1$ is an alkyl chain containing between 1 and 4 carbon atoms, and W is a group of the formula:

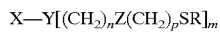
X—Y[(CH$_2$)$_n$Z(CH$_2$)$_p$SR]$_m$ where X is either a carbon, nitrogen or oxygen, Y is a carbon or an alkyl chain of 1–4 carbons or if X is a carbon Y may be a nitrogen, m is between 1 to 3 if Y is a carbon and between 1 to 2 if Y is a nitrogen, where Z is a bond, O, NH, NR$^1$, an amide or ketone, and where n is between 1 and 5 and p is between 2 and 5, unless Y is N, in which case n is between 2 and 5, and where R$^1$is an alkyl chain containing between 1 and 4 carbon atoms, and R is a small group such as any of the following —SH, —SCH$_2$Ph, —SCH$_2$CO$_2$H, —SCH$_2$CH$_2$CO$_2$H, —SCH$_2$CH$_2$OH, —SCH$_2$CH$_2$CH$_2$OH, —SCH$_3$, —SCH$_2$CH$_3$, —SCH$_2$CH$_2$CH$_3$, —SCH2CO$_2$CH$_3$, —SCH$_2$CO$_2$CH$_2$CH$_3$, an alkyl chain containing between 1 and 4 carbon atoms, or an aryl group.

It is further prefered that the attachment group is thiooctic acid or bis-thiooctic acid derivative.

It is further preferred that the attachment group is the cyclic oxidised form of dithiothreitol.

It is further preferred that the attachment group contains one to three bis(4-hydroxymethyl)-1,2-dithiacyclopentane groups.

It is further preferred that the attachment group contains a bis(4-hydroxymethyl)-1,2-dithiacyclopentane groups where the hydrophilic region is attached via one of the 4-hydroxymethyl moieties of the bis(4-hydroxymethyl)-1, 2-dithiacyclopentane and where the other 4-hydroxymethyl moiety may be the hydroxy functionality or may have been further functionalised to a methyl ether, ethyl ether, propyl ether, acetate, or succinate, or a group of the formula (CH$_2$)$_n$COZ where n is 0 to 4, and Z is OR, or NR$^1$R$^2$, where R, R$^1$and R$^2$ are independently hydrogen or alkyl chains containing between 1 and 4 carbon atoms.

It is further preferred that the attachment group contains a bis(4-hydroxymethyl)-1,2-dithiacyclopentane groups where the hydrophilic region is attached via one of the 4-hydroxymethyl moieties of the bis(4-hydroxymethyl)-1, 2-dithiacyclopentane and where the other 4-hydroxymethyl moiety may be linked to between one and three other bis(4-hydroxymethyl)-1,2-dithiacyclopentane groups.

It is further preferred that the linking group be ethyleneoxy or diethyleneoxy.

It is further preferred that the attachment group contains one to three dithiothreitol groups.

It is further preferred that the attachment group contains a trans-4,5-dihydroxy-1,2-dithiacyclohexane groups where the hydrophilic region is attached via one of the 4,5-hydroxy moieties of the trans-4,5-dihydroxy-1,2-dithiacyclohexane and where the other 4,5-hydroxy moiety may be the hydroxy functionality or may have been further functionalised to a methyl ether, ethyl ether, propyl ether, acetate, or succinate, or a group of the formula (CH$_2$)$_n$COZ where n is 0 to 4, and Z is OR, or NR$^1$R$^2$, where R, R$^1$ and R$^2$ are independently hydrogen or alkyl chains containing between 1 and 4 carbon atoms.

It is further preferred that the attachment group contains a trans-4,5-dihydroxy-1,2-dithiacyclohexane groups where the hydrophilic region is attached via one of the 4,5-hydroxy moieties of the trans-4,5-dihydroxy-1,2-dithiacyclohexane and where the other 4,5-hydroxy moiety may be linked to between one and three other trans-4,5-dihydroxy-1,2-dithiacyclohexane groups.

Sulfur containing compounds can be prepared by conventional literature procedures. Cyclic disulfides can also be prepared by conventional literature procedures, however, it is presently preferred that cyclic disulfides are prepared by the cyclisation of a α,ω-disubstituted thiocyanates by treatment with a source of fluoride ion. It is further preferred that the fluoride ion source is tetrabutylammonium fluoride. The reaction is conducted in an organic solvent or mixture of solvents, at a temperature between −70° and 100° C. It is further preferred that the reaction is conducted in aqueous tetrahydrofuran between 0° and 50° C.

Accordingly in a fourth aspect the present invention consists in a method of producing cyclic disulfides, the method comprising reacting an α,ω-disubstituted thiocyanate with a source of fluoride ion.

In a fifth aspect the present invention consists in linker lipids described in the first aspect of the invention which in addition have an ionophore covalently attached to the hydrophobic region of the linker lipid via at least one tethering chain which is long enough such that the attached ionophore may traverse the membrane in such a way that it is still able to transport ions across the membrane.

Typical ionophores may be natural, semi-synthetic or wholly synthetic ionophores such as valinomycin, nonactin, crown ether derivatives, podands, coronands, cryptands, gramicidin.

In a sixth aspect the present invention consists in a membrane formed exclusively from linker lipids of the first aspect of the invention and fourth aspect of the present invention to which are tethered ionophores.

In a seventh aspect the present invention consists in a membrane formed from a plurality of linker lipids according to the first aspect and a plurality of linker lipids according to the second aspect of the invention and additional lipids and ion channels so as to form a membrane that has the similar thickness to a normal bilayer membrane structure.

It is further preferred that the ion channel added to the membrane is a gramicidin derivative that is capable of being linked to a protein such as streptavidin or an antibody or antibody fragment or other receptor molecule.

In a preferred embodiment of this aspect of the present invention the membrane also includes a plurality of linker ion channels according to the third aspect of the invention.

As will be appreciated by those skilled in this field that the membranes of the present invention may include additional lipid. In these instances it is preferred that the additional lipid is a mixture of diphytanyl ether phosphatidyl choline and glycerol diphytanyl ether in a ratio of between 9:1 to 6:4.

Those skilled in the art will also appreciate that where molecules can exist as stereoisomers, that any of the individual stereoisomers, or mixtures thereof, may be employed. In addition, where amines are employed it will be appreciated that common salts of the amines could also be employed.

BRIEF DESCRIPTION OF THE DRAWINGS

In order that the nature of the present invention may be more clearly understood preferred forms thereof will now be described with reference to the following examples and Figures in which:

FIG. 2 shows linker lipid A;

FIG. 3 shows linker gramicidin B;

FIG. 4 shows membrane spanning lipid; and

FIG. 5 shows biotinylated gramicidin E

DETAILED DESCRIPTION OF THE INVENTION

Chemical Syntheses

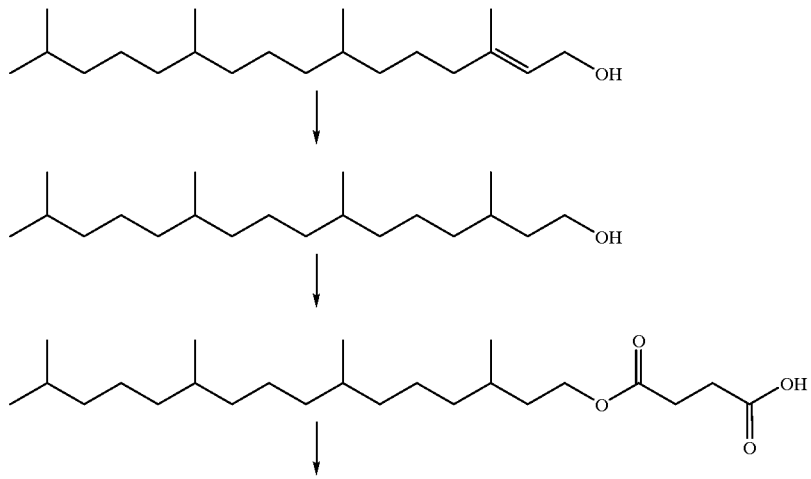

Figure 1:
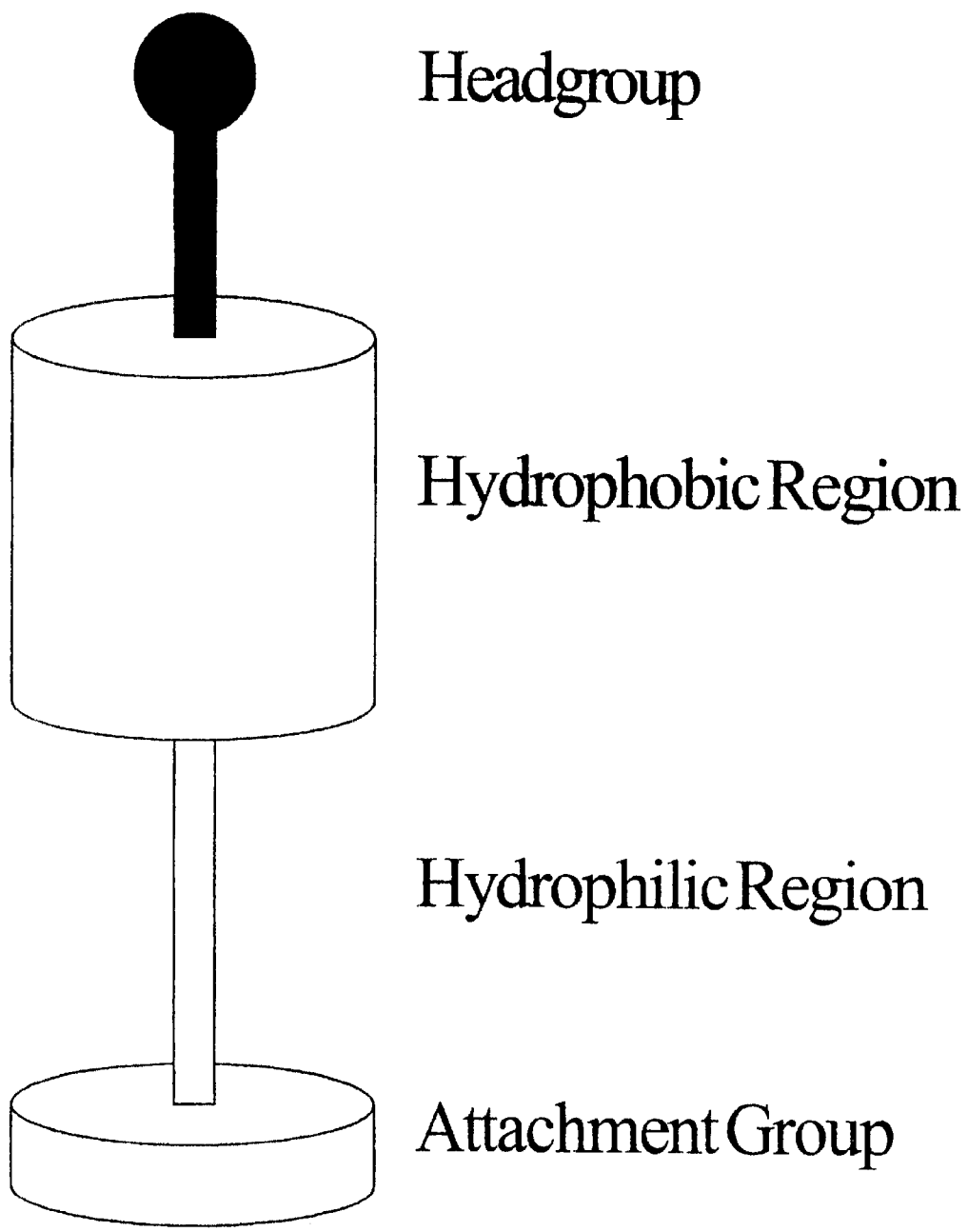
FIG. 1 is a schematic representation of an embodiment of the present invention.

Phytanyl tetraethyleneglycly succinate [(11-hydroxy-3,6,9-trioxa-undecan-1-yl) phytanyl succinate]

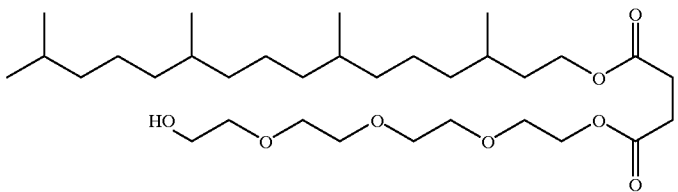

A solution of phytol (49.3 g, 166 mmol) in ethanol (250 ml) was reduced with hydrogen gas at atmospheric pressure over Raney nickel for 3 days. The catalyst was removed by filtration through Celite® and the filtrate concentrated under reduced pressure to give phytanol (49.3 g, 100%). $^1$H-n.m.r. (CDCl$_3$) δ0.84 (m, 15H), 0.90–1.75 (m, 24H), 2.63 (m, 4H), 3.55–3.75 (m, 14H), 4.09 (m, 2H), 4.28 (m, 2H).

purified by flash chromatography (ethyl acetate as eluant) to yield phytanyl (teraethylene glycyl) succinate in 186 mg (68%). $^1$H-n.m.r. (CDCl$_3$) δ0.84 (m, 15H), 0.90–1.75 (m, 24H), 2.63 (m, 4H), 3.55–3.75 (m, 14H), 4.09 (m, 2H), 4.28 (m, 2H).

Phytanyl tripropyleneglycyl succinate [(4,8-dioxa-11-hydroxy-undecan-1-yl) phytanyl succinate]

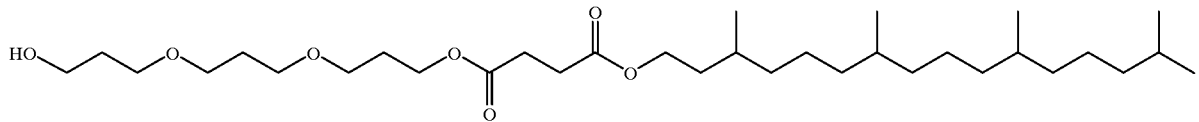

(CDCl$_3$) δ0.8–0.95 (m, 15H), 1.0–1.75 (m, 24H), 3.65–3.75 (m, 2H). $^{13}$C-n.m.r. (CDCl$_3$) δ19.67 (3×Me), 22.60 (Me), 22.69 (Me), 24.36 (CH$_2$), 24.45 (CH$_2$), 24.78 (CH$_2$), 27.95 (CH), 29.50 (CH), 32.76 (2×CH), 37.28–37.43 (m, 5×CH$_2$), 39.35 (CH$_2$), 39.73 and 40.05 (together CH$_2$), 61.18 (CH$_2$).

A mixture of phytanol (5.98 g, 20 mmol) and succinic anhydride (6.0 g) were stirred in dry pyridine (40 ml) under nitrogen for 4 days at room temperature. The mixture was poured into ice-cold hydrochloric acid (2M, 110 ml), the pH adjusted to approximately 3 with additional hydrochloric acid (2M, 50 ml), and the solution extracted with dichloromethane (3×150 ml). The combined organic extracts were washed with hydrochloric acid (1M, 120 ml) and water (200 ml). The final water extract was re-extracted with dichloromethane (100 ml). The combined organic layers were dried (Na$_2$SO$_4$), filtered and the solvent removed under reduced pressure. Phytanyl hemisuccinate was obtained as a colourless oil (7.77 g. 97%). $^1$H-n.m.r. (CDCl$_3$) δ0.8–0.95

To a solution of tripropyleneglycol (prepared following K. Burgess, M. J. Ohlmeyer., *J. Org. Chem.*, 1988, 53, 5179–5181) (2.05 g) and phytanyl hemisuccinate (850 mg) in dry dichloromethane (10 ml), 1-cyclohexyl-3-(2-morpholinoethyl)carbodiimide metho-p-toluenesulfonate (morpho-CDI) (1.08 g), DMAP.HCl (112.5 mg) DMAP (86 mg, 0.71 mmol) was added and the mixture stirred at room temperature for 48 h. The suspension was filtered and the residue washed with dichloromethane (50 ml). The filtrate evaporated and the residue chromatographed (ethyl acetate-:light petroleum 1:1) to give the product (980 mg, 80%) $^1$H nmr (CDCl$_3$) δ0.81–1.27 (m, 39H, phytanyl H), 1.79–1.91 (m, 6H, CH$_2$—CH$_2$—CH$_2$), 2.47 (t, 2H, CH$_2$—SS—Ph), 2.61 (s, 6H, CO—(CH$_2$)$_2$—CO), 3.44–3.54 (m, 4H, CH$_2$—O), 3.61 (t, 2H, CH$_2$—O), 3.76 (t, 2H, CH$_2$—O), 4.11 (t, 2H, CH$_2$—O—CO), 4.17 (t, 2H, CH$_2$—O—CO). m/z 573 (M+H)$^+$.

Phytanyl hexaethyleneglycyl succinate [17-hydroxy-3,6,9,12,15-pentaoxa-h eptadecan-1-yl phytanyl succinate]

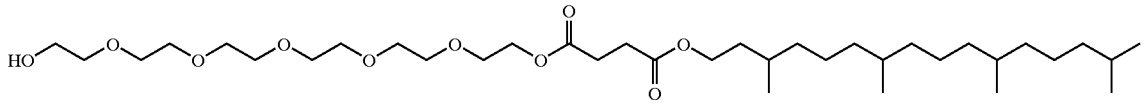

(m, 15H), 0.95–1.80 (m, 24H), 2.55–2.75 (m, 4H), 4.05–4.20 (m, 2H). $^{13}$C-n.m.r. (CDCl$_3$) δ20.1, 20.2, 20.29, 120.36, 20.43, 23.3, 23.4, 25.0, 25.1, 25.5, 28.6, 29.6, 29.7, 30.5, 33.4, 36.1, 36.2, 37.8–38.2, 40.0. 64.2, 172.9, 179.1.

Phytanyl hemisuccinate (0.19 g), tetraethylene glycol (463 mg), DCC (120 mg, 0.16 mmol), DMAP (19 mg, 0.16 mmol), and DMAP.HCl (25 mg) in chloroform (2 ml) were stirred under nitrogen for 70 hours at room temperature. The suspension was filtered, the precipitate washed with dichloromethane, and the combined filtrates were concentrated to dryness under reduced pressure. The residue was Hexaethylene glycol (2.908 g), morpho-CDI (1.070 g), DMAP (0.086 g) and DMAP hydrochloride (0.112 g) were dissolved in dry dichloromethane (9 ml) at room temperature under nitrogen. Phytanyl hemisuccinate (0.840 g) was added dropwise over 10 min. to the stirred solution and the mixture stirred for 4 days. The suspension was filtered and the solid urea washed with dichloromethane. The filtrate was washed with water (20 ml), 1M HCl (20 ml) and brine (20 ml) and the solvent evaporated to give a colourless oil (1.30 g, 93%). Chromatography on silica gel with ethyl acetate as eluant yielded the pure title compound (0.90 g, 64%) as a colourless oil (Found, C, 65.66; H,10.84. C$_{36}$H$_{70}$O$_{10}$ requires C, 65.66; H,10.64%). $^1$H nmr (CDCl$_3$) δ0.75–0.91

(m, 15H, 5×phytanyl Me), 0.91–1.72 (m, 24H, phytanyl), 2.62 (m, 4H, 2×succinate CH$_2$), 3.04 (s, 1H, OH), 3.56–3.73 (m, 22H, 11×HEG CH$_2$), 4.10 (m, 2H, phytanyl OCH$_2$) and 4.23 (m, 2H, HEG CH$_2$OCO); $\delta_C$ (CDCl$_3$) 19.41–19.70 (m), 22.59, 22.67, 24.26, 24.42, 24.75, 27.92, 29.01, 29.07, 29.81, 32.73, 35.40, 35.48, 37.23,7.34, 9.32, 61.67, 63.35, 63.79, 69.12, 70.26, 70.51, 72.48, and 172.29; m/z (M$^+$+1) 663.

under reduced pressure. The resulting pale orange oil was purified by flash chromatography (ethyl acetate) to give triethylene glycol mono tosylate from the most polar fractions as a clear oil (6.94 g, 23%). $^1$H nmr (CDCl$_3$) $\delta$2.44 (s, 3H), 2.56 (br s, 1H OH), 3.56–3.73 (m, 10H), 4.16 (m, 2H), 7.38 and 7.78 (AB quartet, 2H each); $^{13}$C nmr (CDCl$_3$) $\delta$21.33, 42.52, 61.25, 68.31, 69.00, 69.86, 70.36, 72.25, 127.64, 129.63, 144.71; m/z (CI) 305 (M+H)$^+$.

(Phytanyl hexaethyleneglycyl succinate) hemisuccinate [((3,6, 9,12,1 5-pentaoxa-heptadecanyl) phytanyl succinate) hemisuccinate]

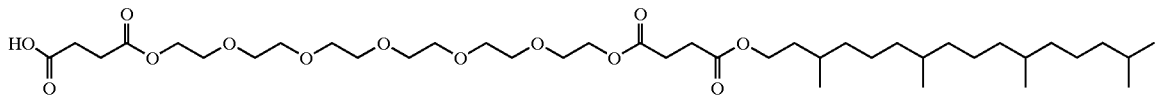

17-Hydroxy-3,6,9,12,15-pentaoxa-heptadecan-1-yl phytanyl succinate (0.80 g) and succinic anhydride (0.361 g) were stirred in dry pyridine (4.5 ml) at room temperature under nitrogen for 45 hours. The mixture was poured into ice-cold hydrochloric acid (2M, 20 ml) and adjusted to pH 3 with further cold acid, extracted with dichloromethane (3×130 ml) and the combined organic layers washed with brine (150 ml), dried (Na$_2$SO$_4$), filtered and the solvent removed to give the title compound (0.84 g, 91%) as a colourless oil which was of high purity by TLC and $^1$H NMR spectroscopy (Found, C, 62.43; H; 10.15. C$_{40}$H$_{74}$O$_{13}$ requires C, 62.97; H, 9.78%). $^1$H nmr (CDCl$_3$) $\delta$0.75–0.94 (m, 15H, 5×phytanyl Me), 0.94–1.75 (m, 24H, phytanyl), 2.62 (m, 8H, 4×succinate CH$_2$), 3.55–3.75 (m, 20H, 10×HEG CH$_2$), 4.12 (m, 2H, phytanyl CH$_2$) and 4.25 (m, 4H, HEG CH$_2$OCO).

1-Bromo-8-(t-butyldimethylsilyloxy)-3,6-dioxa-octane

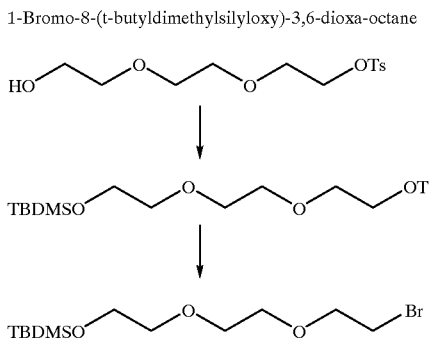

((Diphytanyl)glyceryl hexaethyleneglycyl succinate) hemisuccinate

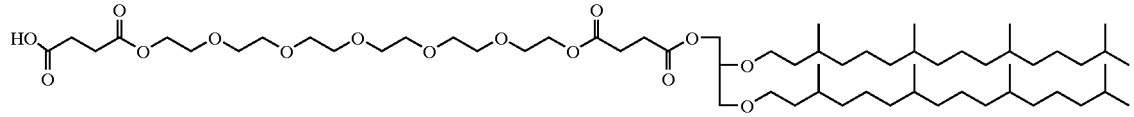

((3,6,9,12,15-Pentaoxa-heptadecanyl) diphytanylglyceryl succinate) hemisuccinate was prepared following the procedure for the synthesis of ((3,6,9,12,15-pentaoxa-heptadecanyl) phytanyl succinate) hemisuccinate, though replacing phytanol with (diphytanyl)glycerol. $^1$H nmr (CDCl$_3$) $\delta$0.75–0.92 (m, 30H, 10×phytanyl Me), 0.92–1.72 (m, 48H, phytanyl), 2.65 (broad s, 8H, 4×succinate CH$_2$), 3.40–3.72 (m, 27H, 13×CH$_2$O and CHO), 4.06–4.32 (m, 6H, 3×CH$_2$OCO).

Triethylene glycol mono tosylate
[1-p-tosyloxy-3,6-dioxa-octan-8-ol]

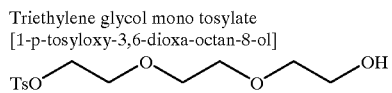

p-Toluenesulfonyl chloride (17.1 g) was added portionwise to triethylene glycol (15 g) in pyridine (600 ml) at 0° C. The solution was allowed to warm to room temperature and stirring continued for 16 h. The solvent was removed under reduced pressure to approximately 50 ml and the residue diluted with hydrochloric acid (100 ml, 3M), extracted with dichloromethane (3×100 ml), washed with brine (150 ml), dried (Na$_2$SO$_4$), and the solvent removed Imidazole (1.68 g, 24.6 mmol) and t-butyldimethylsilyl chloride (2.97 g, 19.7 mmol) in N,N-DMF (45 ml) were stirred at room temperature for 30 min. Triethylene glycol mono tosylate (5 g, 16.4 mmol) in DMF (40 ml) was added and stirring continued for 4 h. The solvent was removed under reduced pressure to approximately 5 ml and the residue diluted with H$_2$O (100 ml), extracted with ether (3×75 ml), washed with brine (100 ml), dried (Na$_2$SO$_4$), and concentrated. The resulting pale yellow oil was purified by flash chromatography (light petroleum-ethyl acetate; 85:15 to 70:30) to give 1-(t-butyldimethylsilyloxy)-3,6-dioxa-8-p-tosyloxy-octane as a clear oil (3.62 g, 52.6%). $^1$H nmr (CDCl$_3$) $\delta$0.08 (s, 6H), 0.88 (s, 9H), 2.44 (s, 3H), (3.54–3.73 (m, 10H), 4.16 (m, 2H), 7.33 and 7.79 (AB quartet, 2H each).

Lithium bromide (1.19 g) was added to 1-(t-butyldimethylsilyloxy)-3,6-dioxa-8-p-tosyloxy-octane (1.92 g) in dry acetone (15 ml) and the solution heated at reflux for 6 hours. The mixture was filtered through flash silica and subsequently washed with light petroleum-ethyl acetate (150 ml, 95:5). The solvent was removed under reduced pressure and the residue dissolved in ethyl acetate (100 ml), washed with brine (2×75 ml), dried (Na$_2$SO$_4$), and concentrated to give 1-bromo-8-(t-butyldimethylsilyloxy)-3,6- dioxa-octane as a clear liquid (1.17 g, 78%). $^1$H nmr (CDCl$_3$) δ0.06 (s, 6H), 0.89 (s, 9H), 3.41–3.86 (m, 12H); $^{13}$C nmr (CDCl$_3$) δ–5.27, 18.36, 25.92, 30.25, 62.72, 70.59, 70.73, 71.22, 72.73; m/z 329, 327 (M+H)$^+$.

product purified by column chromatography (flash silica, 4–10% methanol in dichloromethane). Yield 4.77 g, 70% $^1$H-n.m.r. (CDCl$_3$) δ0.81–1.64 (m, 37H, phyt), 1.93 (m, 2H), 2.19 (m. 2H), 2.79 and 2.81 (s, 3H, NCH$_3$), 5.30 (s(b), 1H, NH); m/z (CI;CH$_4$) 326 (M$^+$), 270.

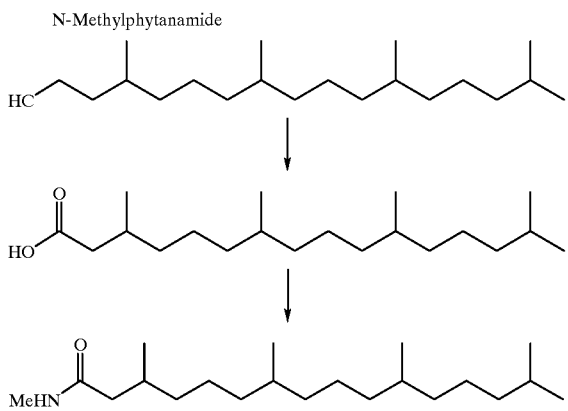

N-Methylphytanamide

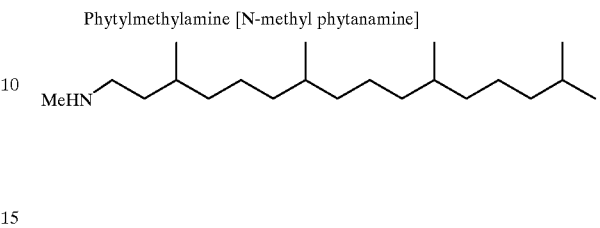

Phytylmethylamine [N-methyl phytanamine]

Phytanol (19.5 g) was dissolved in acetic acid (250 ml) and cooled in an ice bath. Chromium trioxide (21.0 g) dissolved in a minimum amount of water was added to the above solution and stirred at room temperature for 18 hours. Ethanol (50 ml) was slowly added to the reaction mixture and stirred for a further 3 hours. Most of solvent was removed and water (250 ml) was added. This solution was extracted with ether (2×200 ml) and the combined ether extract was dried (MgSO$_4$), decolourized with activated charcoal and filtered through a thin flash silica bed. The solvent was removed and the crude product chromatographed on flash silica (1–4% methanol in dichloromethane) to give phytanoic acid as a pale yellow liquid. Yield 7.03 g, 34%.

Phytanoic acid (6.4 g) was dissolved in thionyl chloride (10 ml) and heated under reflux for 1.5 hours. Excess thionyl chloride was distilled off and the product dried under reduced pressure for one hour. This light yellow liquid was added dropwise into a solution of methylamine in tetrahydrofuran (2M solution in THF, 50 ml) and stirred for 18 hours. Most of the solvent removed under reduced pressure and the product partitioned between water (150 ml) and dichloromethane (100 ml). The organic layer was removed and washed with dilute hydrochloric acid and dried with magnesium sulfate. The solvent was removed and the crude A mixture of N-methylphytanamide (4.0 g) and lithium aluminium hydride (pellets 95%, 2.0 g) in tetrahydrofuran (100 ml) was heated under reflux for two hours. The reaction mixture cooled, excess lithium aluminium hydride destroyed, and solid salts were filtered off. The crude product was dissolved in dichloromethane and washed with water, dried (MgSO$_4$) and the solvent removed. The crude product was chromatographed on flash silica (1% aqueous ammonia, 10–20% methanol in dichloromethane ) to give pure N-methylphytanamine as a colourless liquid. Yield 2.08 g, 54%. $^1$H-n.m.r. (CDCl$_3$) δ0.82–1.5(m, 39H, phyt), 2.439 (s, 3H, NCH$_3$), 2.54 (m, 2H, CH$_2$CH$_2$NH).

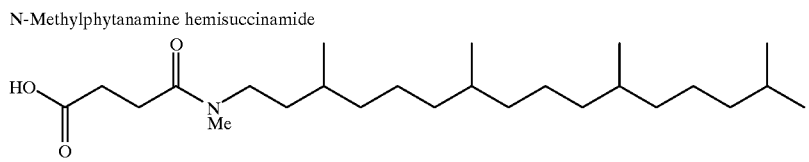

N-Methylphytanamine hemisuccinamide

N-Methylphytanamine (1.0 g) and succinic anhydride (1.0 g) were dissolved in pyridine (5 ml) and stirred at room temperature for 18 hours. The solvent was removed and the crude product dissolved in dichloromethane. This was washed with 2N hydrochloric acid, water and dried (MgSO$_4$). The crude product obtained after removal of solvent was chromatographed on flash silica (methanol 2–5% in dichloromethane) to give pure N-methylphytanamine hemisuccinamide as a colourless liquid. Yield 1.3 g, 100%. $^1$H-n.m.r. (CDCl$_3$) δ0.82–1.55 (m, 39H, phyt), 2.69 (m, 4H, NCOCH$_2$CH$_2$CON), 2.95 and 3.01 (s, 3H, NCH$_3$), 3.25–3.5 (m, 2H, CH$_2$CH$_2$N).

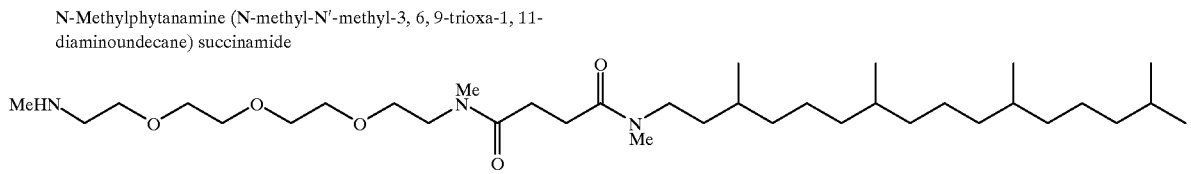

N-Methylphytanamine (N-methyl-N'-methyl-3, 6, 9-trioxa-1, 11-diaminoundecane) succinamide N-Methylphytanamine hemisuccinamide (447 mg), N-methyl-N'-methyl-3,6,9-trioxa-1,11-diaminoundecane (1.2 g) and DCC (270 mg) was dissolved in dry dichloromethane (50 ml) and stirred for 96 hours at room temperature under nitrogen. The white precipitate formed was removed by filtration and the crude product obtained from the filtrate was chromatographed on flash silica (15% methanol in dichloromethane) to give N-methylphytanamine (N-methyl-N'-methyl-tetraethyleneglycylamine) succinamide as a colourless liquid. Yield 313 mg, 69%. $^1$H-n.m.r. (CDCl$_3$) δ0.82–1.55 (m, 39H, Phyt), 2.45 (s(b), CH$_2$NHCH$_3$), 2.64 (m, 4H, NCOCH$_2$CH$_2$CON), 2.76 (m, 2H, CH$_2$NHCH$_3$), 2.91, 2.96, 3.01, 3.11 (s, 6H, CONCH$_3$), 3.36 (m, 2H, phytCH$_2$N), 3.59 (m, 14H, CON(CH$_3$)CH$_2$CH$_2$O—+OCH$_2$CH$_2$O—+O—CH$_2$CH$_2$NH CH$_3$).

added. The mixture was cooled to 0° C. and methanesulfonyl chloride (45 mg) was introduced. This was stirred at room temperature for 24 h. Ether (20 ml) was added and the organic layer washed with a saturated solution of sodium hydrogen carbonate (2×20 ml), water (2×20 ml), dried (MgSO$_4$) and evaporated to give the product (220 mg, 98%). $^1$H-n.m.r. (CDCl$_3$) δ0.82–1.78 (m, 130H, phytanyl and C-15 chain), 3.02 (s, 6H, methyl sulfonate), 3.39–3.68 (m, 14H, CH$_2$—O), 3.97 (t, 4H, CH$_2$—OPh), 4.19–4.39 (m, 4H, —CH$_2$—OSO$_2$Me), 6.93 (d, 4H) 7.45 (d, 4H, aromatic H). m/z (MALDI) 1507 (M$^+$).

(N-Methylphytanamine (N-methyl-N'-methyl-3, 6, 9-trioxa-1, 11-diaminoundecane) succinamide) hemisuccinamide

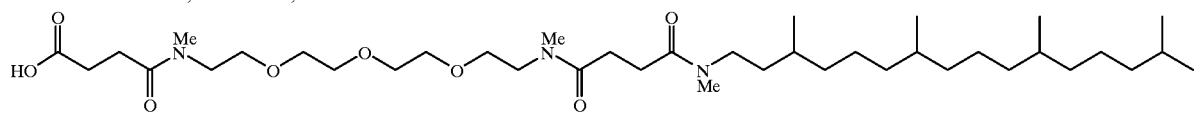

N-Methylphytanamine (N-methyl-N'-methyl-tetraethyleneglycylamine) succinamide (461 mg) and succinic anhydride (200 mg) were dissolved in pyridine (10 ml) and stirred at room temperature for 48 hours. The solvent was removed and the crude product chromatographed on flash silica (1% acetic acid, 15% methanol in dichloromethane) to give pure (N-methylphytanamine (N-methyl-N'-methyl-3,6,9-trioxa-1,11-diaminoundecane) succinamide) hemisuccinamide as a colourless liquid. Yield 530 mg, 100%. $^1$H-n.m.r. (CDCl$_3$) δ0.82–1.55 (m, 39H, Phyt), 2.68 (m, 8H, succinates), 2.91, 2.96, 3.01, 3.09, 3.11 (s, 9H, NCH$_3$), 3.36 (m, 2H, phytCH$_2$N), 3.60 (m, 16H, N(CH$_3$)CH$_2$CH$_2$O—+OCH$_2$CH$_2$O—); m/z (MALDI) 715, 714.

Membrane spanning lipid dimesylate [MSL dimesylate]

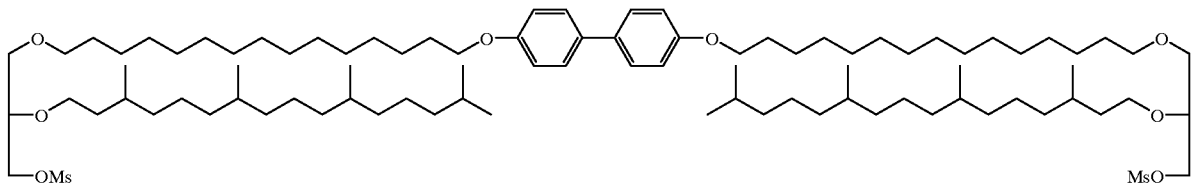

To a solution of 'membrane spanning lipid C' (see FIG. 4, n=4) (200 mg) in THF (7 ml), triethylamine (40 mg) was Membrane spanning lipid diazide [MSL diazide]

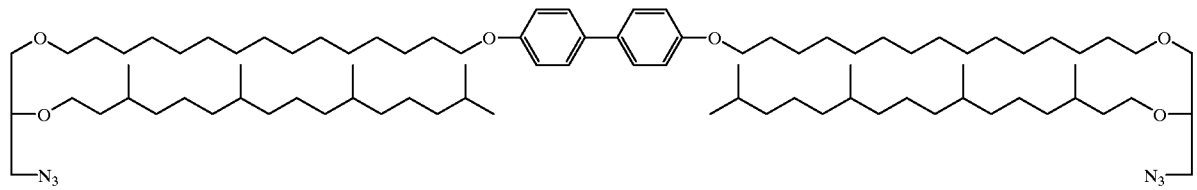

A solution of MSL dimesylate (220 mg) in DMF (10 ml) containing sodium azide (30 mg) was heated at 110° C. for 48 h. Brine (50 ml) was added and the mixture extracted with ether (4×50 ml). The combined ether extract was washed with water (3×50 ml) dried and evaporated to give a waxy solid (195 mg, 95%). $^1$H-n.m.r. (CDCl$_3$) δ0.82–1.79 (m, 130H, phytanyl and C-15 chain), 3.30–3.62 (m, 18H, CH$_2$—O and —CH$_2$—N$_3$), 3.97 (t, 4H, CH$_2$—OPh), 6.93 (d, 4H) 7.45 (d, 4H, aromatic H). m/z (MALDI) 1376 (M$^+$).

ml), washed with water (2×50 ml), dried (MgSO$_4$). The light yellow crude product was chromatographed on flash silica (dichloromethane/hexane as eluant) to yield pure N-phytanyl phthalimide in 11.89 g (80.9%) $^1$H-n.m.r. (CDCl$_3$) δ0.82–1.8 (m, 39H), 3.73 (t, 2H, CH$_2$N), 7.73 (m, 2H, ArH), 7.88 (m, 2H, ArH); m/z 431 (M$^+$).

Phytanyl phthalimide (1.7 g) was dissolved in ethanol (100 ml) and hydrazine hydrate (2 ml) was added and heated under reflux for 2.5 hours. The reaction mixture was cooled Diamino membrane spanning lipid [MSL diamine]

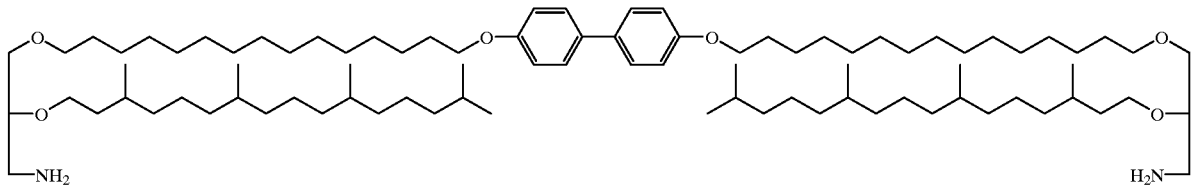

The MSL diazide (400 mg, 0.28 mm) was dissolved in freshly distilled THF (12 ml) and the solution cooled to 0° C. Lithium aluminium hydride (0.4 ml, 1M solution in ether) was introduced and the reaction was stirred at room temperature for 24 h. Water (60 ml) was added and the solution extracted with chloroform (5×50 ml). The combined organic phase was washed with brine (50 ml) dried and evaporated to give the product (260 mg, 67%). $^1$H-n.m.r. (CDCl$_3$) δ0.83–1.56 (m, 130H, phytanyl and C-15 chain), 2.74–2.83 (m, 4H, —CH$_2$—NH2), 3.39–3.65 (m, 14H, CH$_2$—O), 3.98 (t, 4H, CH$_2$—OPh), 6.93 (4H,d) 7.45 (4H,d) (aromatic H). m/z (MALDI) 1348 (M$^+$).

and concentrated hydrochloric acid (1 ml) added. The white precipitate formed was filtered and the filtrate was neutralised with 20% sodium hydroxide. This aqueous solution was extracted, dried with magnesium sulphate and the solvent removed under reduced pressure. This product was used without further purification. $^1$H-n.m.r. (CDCl$_3$) δ0.82–1.8 (m, 39H), 3.65 (t, 2H, NCH$_2$); m/z (CI CH$_4$) 297 (M+H), 283, 281, 225, 211, 197, 183,169, 155, 141, 127, 113, 99, 85, 71.

Phytanamine hemisuccinamide

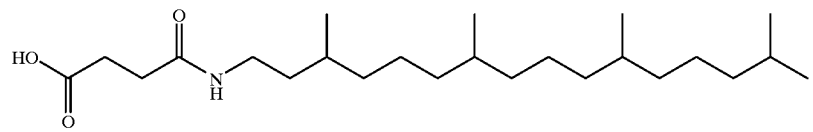

Phytanamine

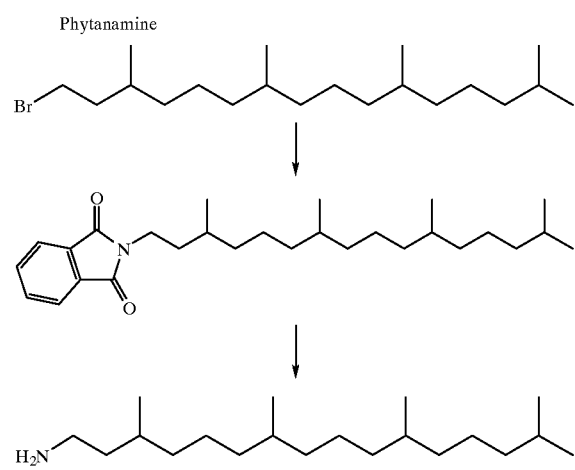

Phytanyl bromide (12.34 g), potassium phthalimide (6.95 g) and DMF (50 ml) were heated at 120–130° C. for 4 hours. Most of the DMF was removed under reduced pressure and the crude product was dissolved in dichloromethane (100

Phytylamine (2.32 g), succinic anhydride (1.16 g) and pyridine (10 ml) was stirred at room temperature for 48 hours. Most of the pyridine was removed under reduced pressure and the crude product dissolved in dichloromethane and washed with 2M HCl (2×100 ml). The organic was layer separated, dried (MgSO$_4$) and concentrated in vacuo to dryness. The crude product was chromotographed (ethyl acetate as eluant) to give phytanamine hemisuccinamide 1.23 g (91%) as a thick liquid which solidified on standing $^1$H-n.m.r. (CDCl$_3$) δ0.8–1.8 (m, 39H), 2.5 (m, 2H, CH$_2$COO—), 2.6 (m, 2H, CH$_2$COOH), 3.2 (m, 2H, CH$_2$N—), 5.79 (b, 1H, NH), m/z (CI, CH$_4$), 412 (M$^+$)

Mono-BOC diamino-tetraethyleneglycol [N-(t-butyloxycarbonyl)-3, 6, 9-trioxa-1, 11-diaminoundecane]

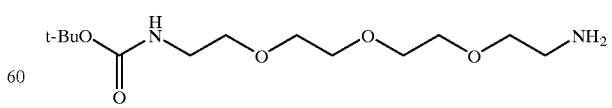

3,6,9-Trioxa-1,11-diaminoundecane (1.03 g), BOC-ON (1.38 g, 5.62 mmol), triethylamine (0.81 g) were dissolved in 1:1 mixture of water and dioxane (40 ml). The reaction mixture was stirred at room temperature for 24 hours and the bulk of the solvent removed under reduced pressure. The crude product was dissolved in water and extracted with dichloromethane (4×100 ml). The combined organic extract was dried (MgSO$_4$) and the solvent removed under reduced pressure to give the crude product as a thick liquid. This was chromotographed on flash silica (20% methanol in dichloromethane as eluant) to give N-(t-butyloxycarbonyl)-3,6,9-trioxa-1,11-diaminoundecane 0.16 g (26%) as a colourless thick liquid. $^1$H-n.m.r. (CDCl$_3$) δ1.44 (s, 9H, $^t$Bu), 2.85 (b, 2H, CH$_2$NH$_2$), 3.31 (m, 2H, CH$_2$NHCOOtBu), 3.30–3.70 (m, 8H, OCH$_2$), 5.4 (b, 1H, CH$_2$NHCOOtBu); m/z 293 (M$^+$), 265, 237, 193.

stand at room temperature for 2 hours. TFA was removed under reduced pressure and the residue was chromatographed as the TFA salt of the amine (flash silica, 2–5% methanol in dichloromethane as eluant). This product was dissolved in dichloromethane and stirred with potassium carbonate to give the free amine as a colourless liquid. 1.33 g, 100%. $^1$H-n.m.r. (CD$_3$OD) δ0.62–1.4 (m, 39H, Phyt), 2.23 (s, 4H, NCOCH$_2$CH$_2$CON), 2.6 (m(b), 2H, —CH$_2$NH$_2$), 2.9–3.4 (m, 16H, CH$_2$NH+NHCH$_2$CH$_2$O—+ OCH$_2$CH$_2$O); m/z (CI, CH$_4$) 572 (M+), 380, 275.

Phytanamine (N-(t-butyloxycarbonyl)-3, 6, 9-trioxa-1, 11-diaminoundecane) succinamide

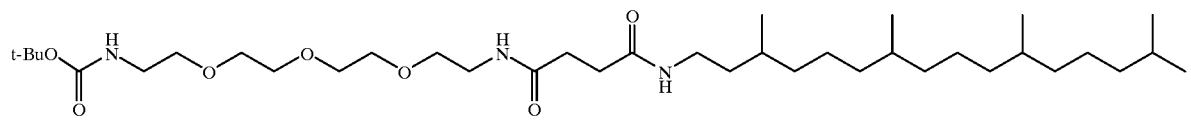

N-(t-butyloxycarbonyl)-3,6,9-trioxa-1,11-diaminoundecane (626 mg), mono-protected diamine (390 mg), morpho-CDI, (733 mg) and DMAP (192 mg) was dissolved in dichloromethane (10 ml) and stirred under nitrogen for 24 hours. The white precipitate formed was filtered and the solvent removed in vacuo. The crude product was chromatographed on flash silica (5–10% methanol in dichloromethane as eluant) to give the product as a thick, light yellow liquid. Yield 403 mg, 71%. $^1$H-n.m.r. (CDCl$_3$) δ0.82–1.55 (m, 48H, phyt+$^t$Bu), 2.52 (m, 4H, NCOCH$_2$CH$_2$CON), 3.22–3.64 (m, 8H, NCH$_2$CH$_2$O+ OCH$_2$CH$_2$O), 5.15 (m, 1H, NH), 6.0 (m, 1H, NH), 6.4 (m, 1H, NH); m/z 673 (M+H)$^+$, 599, 573, 437, 380, 275, 219.

Phytanamine (3, 6, 9-trioxa-1, 11-diaminoundecane) succinamide

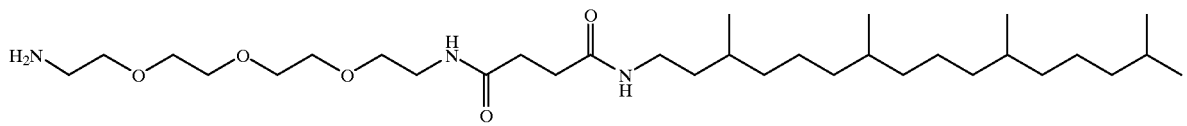

Phytanamine (N-(t-butyloxycarbonyl)-36,9-trioxa-1,11-diaminoundecane)succinamide (1.5 g, 2.23 mmol) was dissolved in trifluoroacetic acid (TFA) (10 ml) and allowed to (Phytanamine (3, 6, 9-trioxa-1, 11-diaminoundecane) succinamide) hemisuccinamide

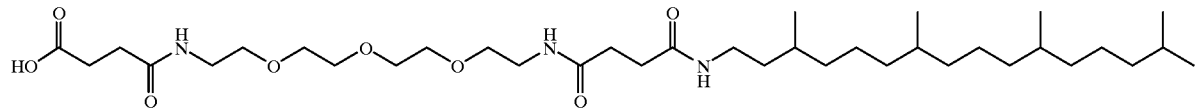

Phytanamine (3,6,9-trioxa-1,11-diaminoundecane) succinamide (1.3 g) was dissolved in pyridine (25 ml) and succinic anhydride (340 mg, 3.4 mmol) was added. The reaction mixture stirred at room temperature for 24 hours and solvent removed. The crude product was chromatographed on flash silica (3–10% methanol in dichloromethane as eluant) to yield pure 1.22 g (80%) (phytanamine (3,6,9-trioxa-1,11-diaminoundecane)succinamide) hemisuccinamide. $^1$H-n.m.r. (CDCl$_3$) δ0.85–1.6 (m, 49H, Phyt), 2.5–2.7 (m, 8H, NCOCH$_2$CH$_2$CON), 3.22 (m, 2H, CH$_2$NH), 3.43 (m, 4H, —OCH$_2$CH$_2$NH—), 3.56 (OCH$_2$CH$_2$NH—), 3.65 (s, 8H, OCH$_2$CH$_2$O—), 6.29 (m, 1H, NH), 6.90 (m, 1H, NH), 7.11 (m, 1H, NH); m/z (CI, CH$_4$) δ55 (M–H$_2$O)$^+$, 380, 298.

Trans-O-Methyldithiothreitol (oxidised form) [4RS, 5RS-4-hydroxy-5-methoxy-1, 2-dithiacyclohexane]

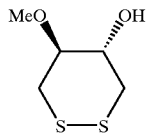

Sodium hydride (276 mg) was added portionwise to a stirred solution of trans 1,2-dithiane-4,5-diol (1 g) in dry THF (50 ml) under N$_2$ over 30 min. After stirring at room temperature for 30 min., methyl iodide (6 ml) was added in 3 equal portions approximately 30 min. apart. After 4 h, the reaction solution was concentrated under reduced pressure to approximately 5 ml and saturated aqueous NH$_4$Cl (10 ml) was added, followed by water (75 ml). The aqueous layer was extracted with dichloromethane (3×60 ml) and the organic layers combined, washed with brine (50 ml) and dried (Na$_2$SO$_4$). The solvent was removed under reduced pressure to give 993 mg of a mixture of mono and di substituted products (91% yield, 75:25 ratio, respectively) as a yellow/cloudy oil. The products were separated by flash column chromatography using Dichloromethane-MeOH (100:0 to 99:1) as eluant to give 4RS,5RS-4-hydroxy-5-methoxy-1,2-dithiacyclohexane from the most polar fractions (600 mg, 60%). $^1$H-n.m.r. (CDCl$_3$) δ2.73 (br s, 1H), 2.83 (dd, 1H), 2.99 (br dd, 1H), 3.05–3.19 (m, 2H), 3.22–3.28 (m, 1H), 3.44 (s, 3H), 3.66–3.73 (m, 1H). $^{13}$C-n.m.r. (CDCl$_3$) δ36.4, 39.9, 56.9, 73.0, 84.1.

4-Hydroxymethyl-4-methoxymethyl-1, 2-dithiacyclopentane

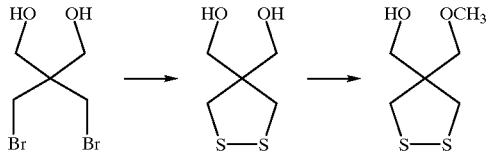

A mixture of sodium sulfide nonahydrate (18 g), sulfur (12 g) and sodium hydroxide (10.4 g) in H$_2$O (120 ml) was heated on a steam bath for 20 min. after which time a solution of 2,2-bis-(bromomethyl)-1,3-propanediol (5.0 g) in ethanol (50 ml) was added. The resulting mixture was refluxed for 3 h, cooled to room temperature and diluted with H$_2$O (500 ml). The solution was extracted (continuous liquid-liquid extraction) with ether and the organic phase dried (Na$_2$SO$_4$). The solvent was removed under reduced pressure to afford a pale yellow crystalline solid which was recrystallised from toluene to give 4,4'-bishydroxymethyl-1,2-dithiacyclopentane as pale yellow plates (1.26 g, 40%); m.p. 129° C. Found: C, 36.4; H, 6.1%. C$_5$H$_{10}$O$_2$S$_2$ requires C, 36.09; H, 6.02%. $^1$H-n.m.r. (CDCl$_3$) δ2.85 (br s, 4H), 3.60 (d, 4H), 4.40 (t, 2H).

A solution of 4,4'-bishydroxymethyl-1,2-dithiacyclopentane (3 g) in THF (40 ml) was added to a suspension of sodium hydride (0.44 g) in THF (15 ml) under nitrogen. The mixture was stirred for 1 h at room temperature and methyl iodide (7.62 g) was added portionwise over 3 h and the resulting mixture was left to stir for 16 h. Water (20 ml) was added and the aqueous layer was extracted with ethyl acetate (5×50 ml). The combined organic layers were washed with brine (3×50 ml) and dried (Na$_2$SO$_4$). The solvent was removed under reduced pressure and the product purified by flash chromatography (ethyl acetate-light petroleum, 1:1 as eluant). 4-Hydroxymethyl-4-methoxymethyl-1,2-dithiacyclopentane was obtained as a crystalline solid (2.4 g, 74%); m.p. 49–50° C. Found: C, 40.1; H, 6.8%. C$_6$H$_{12}$O$_2$S$_2$ requires C, 40.0; H, 6.67%. $^1$H-n.m.r. (CDCl$_3$) δ2.88 (s, 1H), 2.89 (AB quartet, 4H), 3.33 (s, 3H), 3.41 (s, 2H), 3.61 (s, 2H). $^{13}$C-n.m.r. (CDCl$_3$) δ44.5, 56.4, 59.4, 66.9, 76.8.

4-(2-Hydroxyethoxy) methyl-4-methoxymethyl-1, 2-dithiacyclopentane

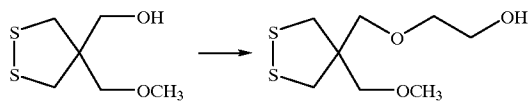

A solution of 4-Hydroxymethyl-4-methoxymethyl-1,2-dithiacyclopentane (0.1 g) in THF (20 ml) was added to a suspension of sodium hydride (0.03 g) in THF (20 ml) and the mixture was stirred at room temperature for 30 min. Ethylene sulfate (0.14 g) was added and the resulting mixture stirred at room temperature for 48 h. Hydrochloric acid (3M, 5 ml) was added, and the aqueous layer extracted with ethyl acetate (5×20 ml). The organic layers were combined and washed with water (50 ml) and dried (Na$_2$SO$_4$). The solvent was removed under reduced pressure and the resulting oil purified by flash chromatography (ethyl acetate-light petroleum, 1:1 as eluant) to give 4-(2-hydroxyethoxy)methyl-4-methoxymethyl-1,2-dithiacyclopentane (66.8 mg, 54%). $^1$H-n.m.r. (CDCl$_3$) δ2.93 (AB quartet, 4H), 3.34 (s, 3H), 3.36 (s, 2H), 3.46 (s, 2H), 3.56 (m, 2H). 3.70 (m, 2H); $^{13}$C-n.m.r. (CDCl$_3$) δ44.7, 56.2, 59.3, 61.6, 72.2, 72.3, 74.2; m/z 224 (M$^+$)

4RS, 5RS-4-(8-t-Butyldimethylsilyloxy-3, 6-dioxa-1-octanyloxy)-5-methoxy-1, 2-dithiacyclohexane

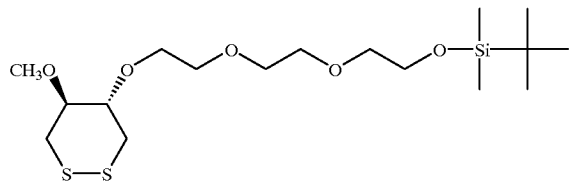

A 60% dispersion of sodium hydride in mineral oil (156 mg) was washed with light petroleum (2×4 ml) and dissolved in THF (7.5 ml). 4RS,5RS-4-Hydroxy-5-methoxy-1, 2-dithiacyclohexane in THF (7.5 ml) was slowly added and the mixture stirred for 15 min. A solution of 1-bromo-8-(t-butyldimethylsilyloxy)-3,6-dioxa-octane in THF (10 ml) was added followed by tetrabutyl ammonium iodide (0.56 g) and stirring continued for 6 days. The solvent was removed under reduced pressure to approximately 5 ml and saturated aqueous $NH_4Cl$ (5 ml) was added followed by $H_2O$ (100 ml). The aqueous phase was extracted with dichloromethane (3×75 ml) and the combined organic phase was washed with brine (100 ml), dried ($Na_2SO_4$), and concentrated. The resulting rust coloured semi-solid was purified by flash chromatography (light petroleum-ethyl acetate; 60:40) to give 4RS,5,RS-4-(8-t-butyldimethylsilyloxy-3,6-dioxa-1-octanyloxy)-5-methoxy-1,2-dithiacyclohexane as a yellow liquid (190 mg, 15.3%). 1H nmr ($CDCl_3$) δ0.06 (s, 6H), 0.88 (s, 9l), 2.73–2.95 (m, 2H), 3.47 (s, 3H), 3.11–3.80 (m, 16H); $^{13}$C-nmr ($CDCl_3$) δ–5.30, 18.32, 25.89, 37.91, 38.39, 58.36, 62.67, 70.41, 70.61, 70.70, 70.88, 72.64, 91.26, 82.19.

concentrated. The resulting pale yellow oil was purified by flash chromatography (ethyl acetate) to give 4RS,5RS-4-(3, 6-dioxa-8-hydroxy-1-octanyloxy)-5-methoxy-1,2-dithiacyclohexane as a rust coloured oil (117 mg, 88.7%). $^1$H nmr ($CDCl_3$) δ2.76–2.94 (m, 3H), 3.13–3.41 (m, 6m), 3.46 (s, 3H), 3.57–3.80 (m, 12H); $^{13}$C nmr ($CDCl_3$) δ37.83, 38.28, 58.22, 61.68, 70.20, 70.30, 70.55, 70.83, 72.52, 81.16, 82.18

(4-(3, 6-Dioxa-8-hydroxy-1-octanyloxy)methyl)-4-methoxymethyl-1 2-dithiacyclopentane

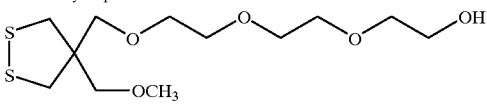

4-(3,6-Dioxa-8-hydroxy-1-octanyloxy)methyl)-4-methoxymethyl-1,2-dithiacyclopentane was prepared following the procedure for the synthesis of 4-(3,6-dioxa-8-hydroxy-1-octanyloxy)-5-methoxy-1,2-dithiacyclohexane, though replacing 4RS,5RS-4-hydroxy-5-methoxy-1,2-dithiacyclohexane with (4-hydroxymethyl-4-methoxymethyl-1,2-dithiacyclopentane. $^1$H nmr ($CDCl_3$) d 2.95 (s, 4H), 3.36 (s, 3H), 3.38 (s, 2H), 3.46 (s, 2H), 3.5–3.8 (m, 12H); m/z 313 (M+H)$^+$.

Mono methoxy dithiane-(triethyleneglycyl succinate tetraethyleneglycyl succinate phytanyl

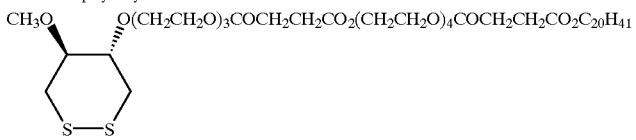

4RS, 5RS-4-(3, 6-Dioxa-8-hydroxy-1-octanyloxy)-5-methoxy-1, 2-dithiacyclohexane

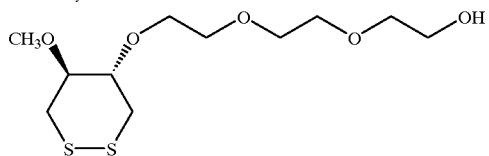

Tetrabutylammonium fluoride (1.1 ml, 1M solution in THF) was added to 4RS,5BS-4-(8-t-butyldimethylsilyloxy-3,6-dioxa-1-octanyloxy)-5-methoxy-1,2-dithiacyclohexane (182 mg) in THF (2.5 ml) at 0° C. and stirred for 5 min, after which time the solution was slowly warmed to room temperature and stirring continued for 24 h. The solvent was removed to approximately 5 ml and the resulting residue diluted with $H_2O$ (50 ml), extracted with dichloromethane (3×40 ml), washed with brine (75 ml), dried ($Na_2SO_4$), and 4RS,5RS-4-(3,6-Dioxa-8-hydroxy-1-octanyloxy)-5-methoxy-1,2-dithiacyclohexane (66 mg) in Dichloromethane (10 ml) was stirred with DMAP (54 mg), DMAP-HCl (71 mg), morpho-CDI (187 mg) and ((3,6,9 -trioxa-undecanyl) phytanyl succinate) hemisuccinate (224 mg) at 0° C. and allowed to slowly warm to room temperature. A white precipitate formed during the initial 24 h and persisted throughout the reaction. After 48 h the mixture was filtered through Celite®. The solvent was removed under reduced pressure and the waxy white residue dissolved in ethyl acetate (75 ml), washed with hydrochloric acid (50 ml, 3M), brine (50 ml), dried ($Na_2SO_4$), and concentrated. The resulting yellow viscous oil was purified by flash chromatography (ethyl acetate) to give mono methoxy dithiane-TREG-Succ-TEGSucc-Phyt as a clear viscous oil (171 mg, 81%); $^1$H nmr ($CDCl_3$) δ0.83 (s, 3H), 0.849 (s,3H), 0.854 (s, 3H), 0.877 (s, 3H), 0.899 (s, 3H), 1.04–1.69 (br m, 24H), 2.61–2.66 (m, 8H), 2.86 (ddd, 2H), 3.18 (br ddd, 2H), 3.27 (m, 1H), 3.39 (m, 1H), 3.47 (s, 3H), 3.61–3.79 (brm, 24H), 4.12 (m, 2H), 4.25 (m, 6H); $^{13}$C nmr (CDCl$_3$) δ19.46, 19.52, 19.68, 19.74, 22.61, 22.70, 24.30, 24.47, 24.78, 27.96, 28.99, 29.06, 29.13, 29.88, 32.77, 35.46, 35.55, 37.28, 37.39, 39.37, 58.35, 63.40, 63.83, 69.08, 70.42, 70.59, 70.96, 172.21; m/z (MALDI) 978 (M+Na$^{30}$)

DMAP (0.011 g) and DMAP:HCl (0.015 g) in dichloromethane at room temperature under nitrogen and stirred for 2 days. The reaction mixture was diluted with water (20 ml) and then extracted with ethyl acetate (4×20 ml) washed with 1M HCl (10 ml), water and brine. The combined ethyl (4-Methoxymethyl-4-triethyleneglycyloxymethyl)-1, 2-dithiacyclopentyl succinate tetraethyleneglycyl succinate phytanyl

(4-Methoxymethyl-4-triethyleneglycyloxymethyl)-1,2-dithiacyclopentyl succinate tetraethyleneglycyl succinate phytanyl was prepared following the procedure for the synthesis of monomethoxy dithiane-(triethyleneglycyl succinate tetraethyleneglycyl succinate phytanyl), though replacing 4RS,5RS-4-(3,6-dioxa-8-hydroxy-1-octanyloxy)-5-methoxy-1,2-dithiacyclohexane with (4-(3,6-dioxa-8-hydroxy-1-octanyloxy)methyl)-4-methoxymethyl-1,2-dithiacyclopentane. $^{1}$H nmr (CDCl$_3$) δ0.84–0.92 (m, 15H), 1.1–1.7 (m, 24H), 2.63 (m, 8H), 2.93 (s, 4H), 3.36 (s, 3H), 3.40 (s, 2H), 3.45 (s, 2H), 3.60–3.75 (m, 22H), 4.1 (m, 2H), 4.25 (m, 6H); m/z (MALDI) 1008 (M$^+$K$^+$).

acetate extracts were dried (Na$_2$SO$_4$). filtered and the solvent removed in vacuo. The organic residue was chromotographed on flash silica with ethyl acetate-light petroleum (1:1) to give 0.15 g (56%) of the title compound as a pale yellow oil. Anal. Calc'd. for C$_{46}$H$_{84}$O$_{13}$S$_2$: C, 59.64; H, 9.2%. Found: C, 59.42; H, 9.57%; $^{1}$H NMR (CDCl$_3$), δ0.83–0.90 (m, —CH$_3$, 15H), 1.23–1.27 (m, —CH$_2$, —CH, 24H), 2.65 (m, CH$_2$COO, 8H), 3.34(s, —OCH$_3$, 3H), 3.35 (s, —OCH$_2$CH$_3$, 2H), 2.99 (AA'BB', 2H), 2.98 (2H), 3.69 (td, 4H), 3.65 (s, —CH$_2$O—, 18H), 4.24 (td, 4H. m/z (MALDI) 925.

(2-(1, 2-Dithiacyclopent-4-yl)-2-methoxymethyl)ethyl-succinate-hexaethyleneglycyl-succinate-phytanyl

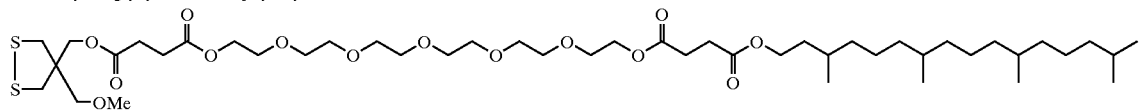

4-Hydroxymethyl-4methoxymethyl-1,2-dithiacyclopentane (0.05 g) was added to a solution of ((3,6,9,12,15-pentaoxa-heptadecanyl) phytanyl succinate) hemisuccinate (0.21 g, 0.28 mmole), morpho-CDI (0.14 g), (2-(1, 2-Dithiacyclopent-4-yl)-2-methoxymethyl)ethyl-succinate-hexaethyleneglycyl-succinate-(diphytanyl)glyceryl

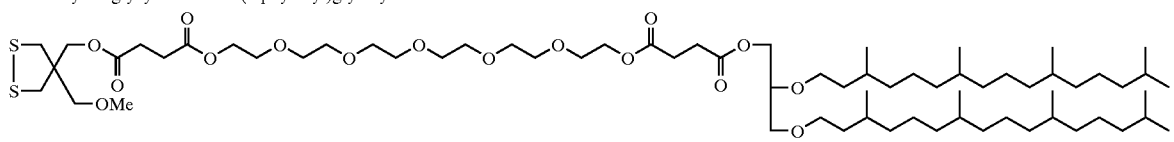

4-Hydroxymethyl-4methoxymethyl-1,2-dithiacyclopentane (0.05 g) was added to a solution of ((3,6,9,12,15-pentaoxa-heptadecanyl) (diphytanyl)glyceryl succinate) hemisuccinate (0.31 g), DCC (0.07 g), DMAP (0.004 g) in dichloromethane at room temperature under nitrogen and stirred for 3 days. The reaction mixture was filtered, and the solvent removed under vacuum. The organic residue was chromatographed on flash silica (ethyl acetate-light petroleum, 1:1, then 100% ethyl acetate) to give 0.22 g (63%) of the title compound as a yellow oil. Anal. Calc'd. For $C_{69}H_{130}O_{16}S_2$: C,64.75; H, 10.24%. Found: C, 64.54; H, 10.42%; $^1$H NMR (CDCl$_3$), δ0.80–0.84 (m, —CH$_3$, 30H), 1.05–1.6 (m, —CH$_2$,—CH, 48H), 2.63 (m, CO—CH$_2$—CH$_2$—CO, 8H), 2.94 (s, S—CH$_2$, 4H), 3.31 (s, —OCH$_3$), 3.33 (s, —CH$_2$OCH$_3$, 2H), 3.45 (m, glyc. CH$_2$, 4H), 3.62 (m,—OCH$_2$CH$_2$O—, 20H), 3.69 (m, —CH$_2$O, 4H), 4.13 (m, CH$_2$O—, 4H). 4.14 (s, —CH$_2$OC=O, 2H), 4.24 (m, COOCH$_2$—, 4H); m/z (ES) 1279.

nitrogen and stirred for 2 days. The reaction mixture was diluted with water (20 ml) and then extracted with ethyl acetate (20 ml×4), washed with 1M HCl (10 ml), water and brine. The combined ethyl acetate extracts were dried over sodium sulfate. filtered and the solvent removed under vacuum. The organic residue was chromotographed on flash silica with ethyl acetate to give the title compound 0.12 g (42%) as a pale yellow oil. Anal. Calc'd. For $C_{45}H_{82}O_{14}S_2$: C, 59.31; H, 9.07%. Found: C, 59.09; H, 9.08%; $^1$H NMR (CDCl$_3$), δ0.83–0.90 (m, —CH$_3$, 15H), 1.23–1.27 (m, —CH$_2$,—CH, 24H), 2.61–2.68 (m, CO—CH$_2$—CH$_2$—CO, 8H), 2.93 (s, S—CH$_2$, 4H), 3.53 (s, —CH$_2$OH, 2H), 3.65 (s, —OCH$_2$CH$_2$O—, 16H), 3.68–3.71 (m, CH$_2$—O, 4H), 4,12 (m, —CH$_2$OO, 4H), 4.20(s, —CH$_2$OC=O, 2H), 4.24 (td, COO—CH$_2$—CH$_2$, 4H); m/z 910 (M$^+$).

(2-(1, 2-Dithiacyclopent-4-yl)-2-hydroxymethyl)ethyl-succinate-hexaethyleneglycyl-succinate-phytanyl

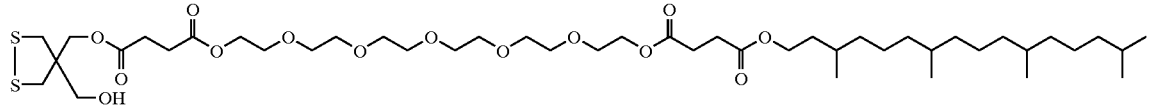

4,4-Bishydroxymethyl-1,2-dithiacyclopentane (0.05 g) was added to a solution of ((3,6,9,12,15-pentaoxa-heptadecanyl) phytanyl succinate) hemisuccinate (0.228 g), morpho-CDI (0.15 g), DMAP (0.011 g) and DMAP:HCl (0.016 g) in dichloromethane at room temperature under Mercaptoacetic acid disulfide diester of (2-(1, 2-Dithiacyclopent-4-yl )-2-hydroxymethyl)ethyl-succinate-hexaethyleneglycyl-succinate-phytanyl

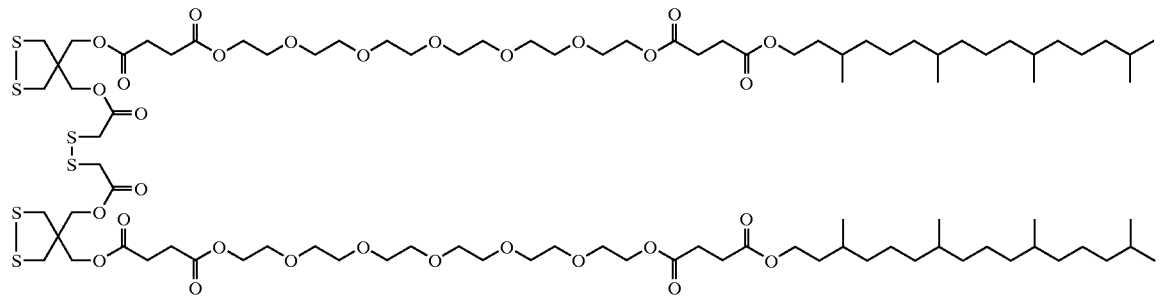

Mercaptoacetic acid disulfide (0.01 g) was added to a solution of (2-(1,2-dithiacyclopentyl)-2-hydroxy)ethyl-succinate-hexaethyleneglycyl-succinate-phytanyl (0.1 g)

morpho-CDI (0.056 g), DMAP (0.0045 g), DMAP.HCl (0.0058 g) in dichloromethane at room temperature under nitrogen and stirred for 2 days. The reaction mixture was diluted with water (20 ml) and then extracted with ethyl acetate (5×20 ml), washed with 1M HCl (10 ml) water and brine. The combined ethyl acetate extracts were dried over sodium sulfate, filtered and the solvent removed under vacuum. The crude oil was chromatographed on flash silica (ethyl acetate) to give 10 mg of pure compound. m/z (MALDI) 1992 (M+Na$^+$).

ml) and the resultant crystalline precipitate isolated by filtration and dried to give 2,2,2-tris-(thiocyanatomethyl) ethyl hemisuccinate as a colourless solid (0.30 g, 84%). $^1$H-n.m.r. (d$_6$-DMSO) δ2.5–2.7 (m, 4H), 3.53 (s, 6H), 4.24 (s, 2H). $^{13}$C-n.m.r. (d$_6$-DMSO) δ28.8, 29.0, 37.2, 44.0, 64.4, 113.1, 171.4, 173.5.

2, 2, 2-tris-(Thiocyanatomethyl)ethyl-succinate-hexaethyleneglycyl-succinate-phytanyl

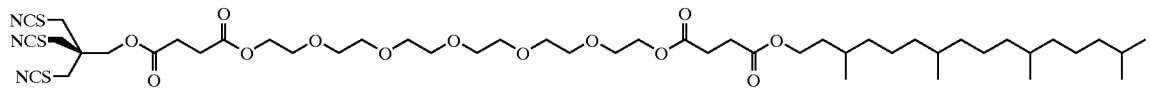

2, 2, 2-tris-(Thiocyanatomethyl)ethyl hemisuccinate

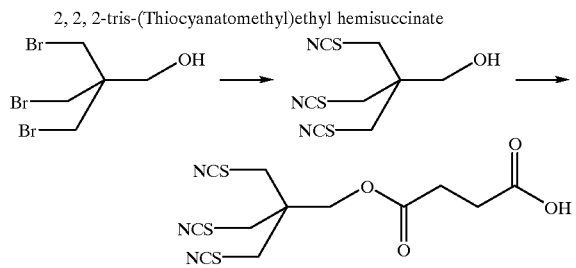

Tribromoneopentyl alcohol (4.72 g) was added to a solution of potassium thiocyanate (8.5 g) in DMF (15 ml) at 100° C. under N$_2$. The solution was heated at 140° C. for 30 min. then stirred for 16 hours at room temperature. The resulting suspension was diluted with H$_2$O (150 ml) and extracted with ether (3×100 ml). The combined ether layers were washed with brine (2×200 ml), dried (Na$_2$SO$_4$) and the solvent removed under reduced pressure. Recrystallisation from CHCl$_3$ gave tris(thiocyanato)neopentyl alcohol as colourless needles (3.05 g, 81%); m.p. 80–81° C. $^1$H-n.m.r. (d$_6$-DMSO) δ3.34 (s, 6H), 3.56 (d, 2H), 5.57 (t, 1H); $^{13}$C-n.m.r. (d$_6$-DMSO) δ37.5, 45.0, 63.3, 113.6.

A solution of tris(thiocyanato)neopentyl alcohol (0.26 g) and succinic anhydride (0.15 g) in dry pyridine (2 ml) was stirred at room temperature under nitrogen for 3 days. The reaction mixture was poured into hydrochloric acid (1M, 10 ml ) and extracted with Dichloromethane (3×40 ml). The combined organic layers were washed with H$_2$O (4 ml) and the aqueous washings re-extracted with Dichloromethane (2.5 ml). The combined organic extracts were dried (Na$_2$SO$_4$), filtered and the solvent removed under reduced pressure. The oily residue was stirred with chloroform (10

2,2,2-tris-(Thiocyanatomethyl)ethyl hemisuccinate (0.675 g) and 17-hydroxy-3,6,9,12,15-pentaoxa-heptadecan-1-yl phytanyl succinate (125 g) were suspended in dry dichloromethane (70 ml) at room temperature under nitrogen . A mixture of morpho-CDI (1.593 g), DMAP (0.689 g) and DMAP.HCl (0.6 g) was added in solid form to the above stirred suspension, to form a colourless solution. Stirring was continued under nitrogen for 4 days, during which time a crystalline solid precipitated. The reaction mixture was washed with water (2×70 ml), 1M HCl (70 ml) and brine (70 ml), dried (Na$_2$SO$_4$), filtered and the solvent removed at 35° C. to give a pale yellow oil (1.90 g, 100%). Chromatography on silica gel with ethyl acetate as eluant yielded the pure title compound (1.79 g, 90%) as an extremely viscous colourless oil. $^1$ H-n.m.r. (CDCl$_3$) δ0.75–0.91 (15H, m, 5×phytanyl Me), 0.91–1.70 (24H, m, phytanyl), 2.58–2.76 (8H, 4×succinate CH$_2$), 3.34 (6H, s, 3×CH$_2$S), 3.59–3.72 (20H, m, 10×HEG CH$_2$), 4.10 (2H, m, phytanyl OCH$_2$), 4.24 (4H, m, 2×HEG CH$_2$OCO), and 4.32 (2H, s, OCH$_2$); $^{13}$C-n.m.r. (CDCl$_3$) δ19.42–19.66 (m, 3×Me), 22.60 (Me), 22.69 (Me), 24.28 (CH$_2$), 24.44(CH$_2$), 24.76 (CH$_2$), 27.94 (CH), 29.02 (m, CH$_2$OCO), 29.83 (CH), 32.74 (CH), 35.41 and 35.49 (phytanyl 2-CH$_2$), 36.70 (CH$_2$), 37.24 (CH$_2$), 37.34 (CH$_2$), 39.73 (CH$_2$), 45.62 (quaterary), 63.25 (CH$_2$O), 63.38 (CH$_2$O), 63.79 (CH$_2$O), 64.17 (CH$_2$O), 68.90 (CH$_2$), 69.03 (CH$_2$), 70.53 (CH$_2$O), 111.17 (SCN), 171.52 (CO), 172.31 (CO), and 172.46(CO); m/z (MALDI) 1028, 1029. (M+Na$^+$ requires 1027).

(2-(1, 2-Dithiacyclopentyl)-2-thiocyanatomethyl)ethyl-succinate-hexaethyleneglycyl-succinate-phytanyl

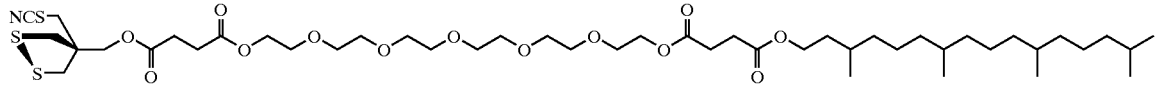

2,2,2-tris-(Thiocyanatomethyl)ethyl-succinate-hexaethyleneglycyl-succinate-phytanyl (0.592 g) was dissolved in dry tetrahydrofuran (4.5 ml) and chilled to 0° C. under nitrogen. Tetrabutylammonium fluoride (0.59 ml 1M solution in THF) was added with stirring over 15 min at 0°

C. and the red solution stirred for 5 min at 0° C., then at room temperature for 48 h. The mixture was diluted with ethyl acetate (30 ml), washed with water (2×15 ml), dried (Na$_2$SO$_4$), filtered and the solvent removed at 40° C. to give a red oil (0.55 g, 98%). Chromatography on silica gel, eluting with light petroleum/ethyl acetate mixtures, yielded the title compound (0.47 g, 84%) as a pale yellow oil. $^1$H-n.m.r. (CDCl$_3$) δ0.75–0.95 (m, 15H, 5×phytanyl Me), 0.95–1.75 (m, 24H, phytanyl), 2.69–2.72 (m, 8H, 2×succinate CH$_2$), 3.09 (s, 4H, CH$_2$SSCH$_2$), 3.33 (s, 2H, CH$_2$SCN), 3.58–3.74 (m, 20H, 10×HEG CH$_2$), 4.12 (m, 2H, phytanyl OCH$_2$), 4.24 (m, 4H, 2×HEG CH$_2$OCO) and 4.27 (s, 2H, OCH$_2$); $^{13}$C-n.m.r. (CDCl$_3$) δ19.43–19.72, (m, 3×Me), 22.59 (Me), 22.69 (Me), 24.27 (CH$_2$), 24.44 (CH$_2$), 24.76 (CH$_2$), 27.93 (CH), 28.88–29.09 (m, CH$_2$OCO), 29.83 (CH), 32.74 (CH), 35.41 and 35.49 (phytanyl 2-CH$_2$), 37.24 (CH$_2$), 37.35 (CH$_2$), 39.33 (CH$_2$), 39.65 (CH$_2$), 45.88 (CH$_2$S), 56.46 (quaternary), 63.37 (CH$_2$O), 63.79 (CH$_2$O), 64.03 (CH$_2$O), 65.85 (CH$_2$O), 68.97 (CH$_2$O), 69.03 (CH$_2$O), 70.55 (CH$_2$O), 112.07 (SCN), 171.62 (CO), 172.20 (CO) and 172.29 (CO): m/z (MALDI) 975; (M +Na$^+$) requires 975; m/z (DCI in NH3) 970; (M+NH$_4^+$).

(2-(1, 2-Dithiacyclopentyl)-2-thiomethyl)ethyl-succinate-hexaethylen eglycyl-succinate-phytanyl) disulfide

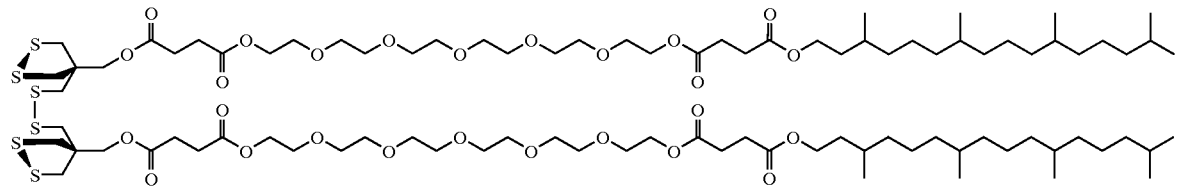

2-(1,2-Dithiacyclopentyl)-2-thiocyanatomethyl)ethyl-succinate-hexaethyleneglycyl-succinate-phytanyl (0.36 g) was dissolved in dry tetrahydrofuran (1.6 ml) under nitrogen at room temperature. Tetrabutylammonium fluoride (0.57 ml 1M solution in THF) was added slowly with stirring and the mixture stirred for 17 h. A further 0.5 eq. of TBAF was added (total 2.0 eq) and stirring continued for an additional 3 h. The mixture was diluted with ethyl acetate (40 ml), washed with water (2×20 ml), dried (Na$_2$SO$_4$), filtered and the solvent evaporated at 40° C. to give a red-brown oil (0.36 g). Chromatography on silica gel with ethyl acetate as eluant afforded the title compound as a pale yellow oil (0.24 g, 69%). $^1$H-n.m.r. (CDCl$_3$) δ0.75–0.92 (m, 30H, 5×phytanyl Me), 0.92–1.73 (m, 48H, phytanyl), 2.56–2.67 (m, 16H, 8×succinate CH$_2$), 2.93–3.18 (m, 12H, 3×CH$_2$SSCH$_2$), 3.55–3.70 (m, 40H, 20×HEG CH$_2$), 4.08 (m, 4H, phytanyl OCH$_2$) and 4.14–4.26 (m, 12H, 4×HEG CH$_2$OCO and 2×OCH$_2$); $^{13}$C-n.m.r. (CDCl$_3$) δ19.34–19.64, (m, Me), 22.51 (Me), 22.60 (Me), 24.16 (CH$_2$), 24.33 (CH$_2$), 24.66 (CH$_2$),27.83 (CH), 28.77–28.98 (m, CH$_2$OCO), 29.72 (CH), 32.63 (CH), 35.31 and 35.39 (phytanyl 2-CH$_2$), 37.13 (CH$_2$), 37.24 (CH$_2$), 39.23 (CH$_2$), 45.74 (CH$_2$S), 46.19 (CH$_2$S), 55.30 (quaternary), 63.24 (CH$_2$O), 63.67 (CH$_2$O), 63.85 (CH$_2$O), 66.35 (CH$_2$O), 68.92 (CH$_2$O), 70.43 (CH$_2$O), 171.55 (CO). 172.02 (CO) and 172.18 (CO); m/z (MALDI) 1876; 927;(M +Na$^+$) requires 1875; $^M/_2$ requires 926.

Below are representative impedance results for the derivatives synthesised above:

EXAMPLE 1

The structure of "linker lipid A" is shown in FIG. 2; the structure of "linker gramicidin B" is shown in FIG. 3; the structure of "membrane spanning lipid D" is shown in FIG. 4; the structure of "membrane spanning lipid C" where n=4 is shown in FIG. 4; the structure of "biotinylated gramicidin E" where n=5, is shown in FIG. 5.

A glass slide or plastic support was evaporatively coated with a 200 Å chromium adhesion layer, followed by a 1000 Å layer of gold. The gold coated substrate was placed in a 50 ml ethanolic solution containing the components as listed in Table 1, in the concentrations shown.

TABLE 1

| COMPONENT | MOLARITY |
| --- | --- |
| Linker lipid A | 370 μM |
| Mercaptoacetic acid Disulfide | 185 μM |
| Membrane spanning lipid C (where n = 4) | 27.75 nM |
| Membrane spanning lipid D | 5.55 μM |
| Linker gramicidin B | 55.5 nM |

The gold coated substrate is preferably placed into this solution within five minutes of preparation. The gold coated substrate is left in this solution for 60 minutes, and then rinsed copiously with ethanol, and then immersed in ethanol for 2–3 hours. The gold slide is then rinsed with ethanol and is assembled in an electrode holder such that an electrode is defined. that for the current examples has an area of approximately 11 mm$^2$. Then, 10 μl of an ethanolic solution of 1,2-di(3RS,7R,11R-phytanyl)-glycero-3-phosphocholine and 1,2-di(3RS,7R,11R-phytanyl)glycerol in a 7:3 ratio, 3 mM total lipid concentration, containing biotinylated gramicidin E where n=5, in a concentration such that the ratio of total lipid to gramicidin derivative is 67,000:1 is added to the surface of the gold electrode and then rinsed with three washes of 150 μl PBS, leaving 100 μl PBS above the electrode surface. A counter electrode, typically silver, is immersed in the PBS solution; and the counter electrode and the sensing electrode are connected to an impedance bridge. A DC offset of −300 mV is applied to the sensing electrode during AC measurement. Then 5 μl of 0.1 mg/ml solution of streptavidin is added to the electrode well, left for three to five minutes, and rinsed with PBS (3×150 μl). Biotinylated anti-ferritin Fab's (5 μl of 0.05 mg/ml solution in PBS), is then added and after three to five minutes the electrode well rinsed with PBS. The biotinylated Fab's were biotinylated via the free thiol group of freshly cleaved (Fab)$_2$ dimers. The response to 100 μl of a 200 pM solution of ferritin is then monitored via impedance spectroscopy.

The new feet were examined individually by replacing linker lipid A and mercaptoacetic acid disulfide in the first layer solutions with the new sulfur containing compound. Identical quantities and methods of addition of the second layer solution, streptavidin and ferritin allowed for direct comparison with the conventional bilayer biosensor.

Selected examples of the advantages of the new feet are illustrated below.

EXAMPLE 2

A first layer solution was prepared using the same concentrations of components as tabulated in Table 1 except replacing linker lipid A with the compound shown directly below in the same concentration, and removing mercaptoacetic acid disulfide from the solution. The assembly was then completed as described in example 1.

TABLE 3

| Preparation | Freq @ phase min. |
|---|---|
| Example 1 | 44 |
| Example 2 | 193 |

EXAMPLE 4

A first layer solution was prepared using the same concentrations of components as tabulated in Table 1 except replacing linker lipid A with the compound shown directly below in the same concentration, and removing mercaptoacetic acid disulfide from the solution. The assembly was then completed as described in example 1.

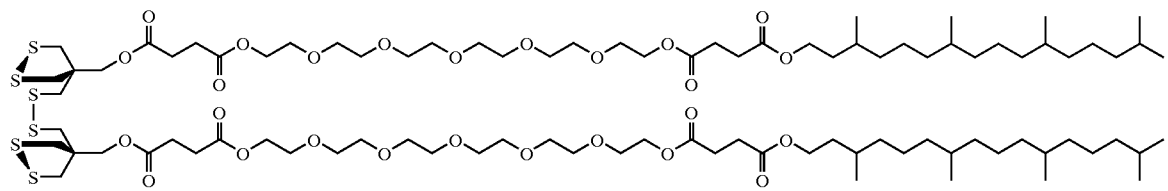

The ferritin gating experiment employing this bigfoot derivative shows similar gating response (see Table 2) to that obtained for the system described in example 1.

TABLE 2

| Preparation | Gating response to Ferritin |
|---|---|
| Example 1 | 48 ± 4% |
| Example 2 | 49 ± 4% |

EXAMPLE 3

A first layer solution was prepared using the same concentrations of components as tabulated in Table 1 except replacing linker lipid A with the compound shown directly below in the same concentration, and removing mercaptoacetic acid disulfide from the solution. The assembly was then completed as described in example 1.

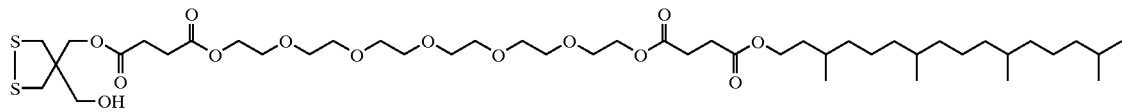

The bilayer membrane obtained using this bigfoot derivative yields a more conductive membrane compared to the system prepared in Example 1 (see Table 3). It is noteworthy that the absence of mercaptoacetic acid from the first layer solution described in Example 1 generates bilayer membranes with lower conductivity compared to that obtained for Example 1 and Example 3.

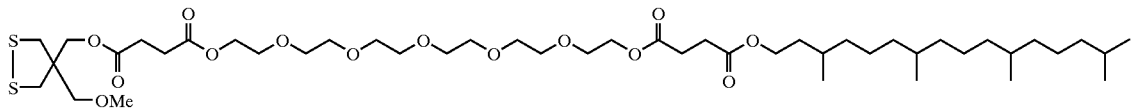

The ferritin gating experiment employing this bigfoot derivative shows a reduced gating response time compared to the assembly described in Example 1 (see Table 4).

TABLE 4

| Preparation | Tau for response to Ferritin |
| --- | --- |
| Example 1 | 190 |
| Example 4 | 56 |

EXAMPLE 5

A first layer solution was prepared using the same concentrations of components as tabulated in Table 1 except replacing linker lipid A with the compound shown directly below in the same concentration. The assembly was then completed as described in Example 1.

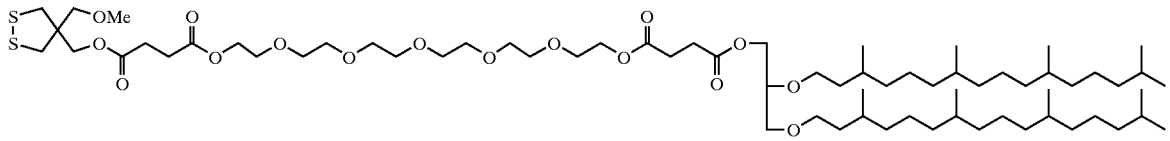

The ferritin gating experiment employing this bigfoot derivative shows a significantly reduced gating response time compared to the assembly described in Example 1 (see Table 5).

TABLE 5

| Preparation | Tau for response to Ferritin |
| --- | --- |
| Example 1 | 190 |
| Example 5 | 38 |

EXAMPLE 6

A gold coated substrate, prepared as described in Example 1, was immersed for 1 hour in a 1 mM ethanolic solution of the bigfoot derivative shown below.

The gold coated substrate should preferably be placed into this solution within five minutes of preparation. The gold coated substrate was left in this solution for 60 minutes, and then rinsed copiously with ethanol, and then immersed in ethanol for 2–3 hours. The gold slide was then rinsed with ethanol, dried in the air, and then mounted in a ultra high vacuum chamber of an Escalab 200 IXL X-ray Photoelectron Spectrometer (XPS). The gold coated substrate was then exposed to monochromatic X-ray irradiation of 1464 eV at ~45° to the surface. The energy spectrum was recorded normal to the surface and the carbon (C 1s), oxygen (O 1s), sulfur (S $p_{1/2}$ and S $p_{3/2}$) and gold (Au $4f_{7/2}$) spectra were recorded.

It was found that four of the six sulfur atoms of the bigfoot derivative were adsorbed to gold. Further, it was found that no qualitative change in the XPS spectrum was apparent after the gold coated substrates with the bigfoot derivative adsorbed to the surface, were immersed in ethanol at 50° for 1 hour. In contrast, when this experiment was repeated replacing the bigfoot derivative with linker lipid A, approximately 30% of linker lipid A desorbed under these conditions.

The present invention provides compounds in which a spacer molecule is covalently incorporated into a linker lipid and/or linked to membrane spanning lipid. This serves several functions.

(A) The space between the hydrophilic chains of the reservoir linker lipid are defined by the size and structure of the binding site on the linker lipid and the packing of the linker lipid on the surface. Thus the spacing is not defined by the ratio of spacer to linker lipid as disclosed in WO 94/07593.

(B) The packing of the hydrophobic chains in the bilayer or monolayer membranes will also be influenced by the density of spacing of the linker lipids. This in turn can influence ionophore conductivity, ionophore diffusion or ionophore gating in the bilayer or monolayer membrane.

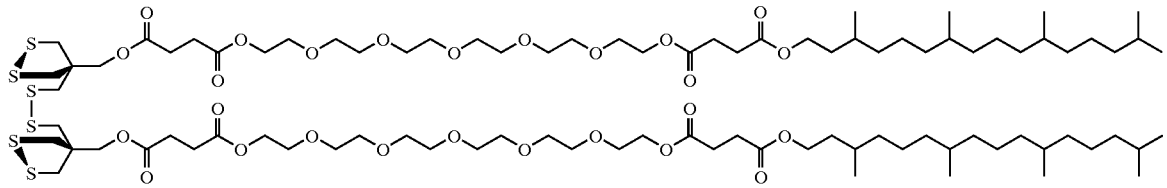

39

(C) There may exist substrates where, on binding of two species onto said substrate phase separation of the two species could occur leading to inhomogeneous distribution of the two species. This inhomogeneous distribution of spacer and linker lipid would in turn lead to inhomogeneous ion reservoir characteristics such as ion capacity or lateral resistivity. This would be avoided by use of the present invention.

(D) Increasing the number of binding interactions between the linker lipid and the substrate would lead to stronger binding between the substrate and the linker lipid and thus lead to a more stable biosensor membrane.

The use of a spacer molecule covalently linked to an ion channel serves the function of creating a space underneath the ion channel such that no other linker lipids can absorb underneath the ion channel. If the ion channel is significantly sterically crowded by other linker lipids then this may influence its ability to assume the appropriate conformation needed in order to form conducting channels. Additionally, the length of time that the channels exist in the open form may also be influenced by steric crowding of the linker lipid. Thus it may be useful for some applications to match the diameter of the binding group with the diameter of the ion channel.

In addition, the present invention provides molecules that include a covalently linked ionophore coupled onto the membrane spanning lipid or the linker lipid. The covalent attachment of the ionophore to the tethered linker lipid serves to prevent it from being removed out of the membrane, while the proper binding site size of the linker lipid ensures that the membrane and reservoir are spaced apart at the appropriate distance to allow proper ionophore conduction.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

What is claimed is:

1. A linker lipid for use in attaching a membrane including a plurality of ionophores to an electrode and providing a space between the membrane and the electrode in which the membrane is either in part or totally made up of the linker lipid, the linker lipid comprising within the same molecule a hydrophobic region spanning the membrane, an attachment group used to attach the molecule to an electrode surface, a hydrophilic region intermediate said hydrophobic region and the attachment group, and a polar head group region attached to the hydrophobic region at a site remote from the hydrophilic region wherein said attachment group has a cross sectional area greater than the cross sectional area of the hydrophilic region, said attachment group having the following structure:

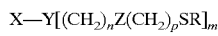

where X is either a carbon, nitrogen or oxygen to which the hydrophilic region is attached, Y is a carbon or if X is a carbon Y is a nitrogen, m is between 1 to 3 if Y is a carbon and between 1 to 2 if Y is a nitrogen, where Z is O, NH, $NR^1$, an amide or ketone, and where n is between 1 and 5 and p is between 2 and 5, unless Y is N, in which case n is between 2 and 5, and where $R^1$ is an alkyl chain containing between 1 and 4 carbon atoms, and R is —SH, —$SCH_2Ph$, —$SCH_2CO_2H$, —$SCH_2CH_2CO_2H$, —$SCH_2CH_2OH$, —$SCH_2CH_2CH_2OH$, —$SCH_3$, —$SCH_2CH_3$, —$SGH_2CH_2CH_3$, —$SCH_2CO_2CH_3$, —$SCH_2CO_2CH_2CH_3$, an alkyl chain containing between 1 and 4 carbon atoms, or an aryl group.

2. A linker lipid as claimed in claim 1 in which the attachment group has a cross sectional area at least 1.5 times the cross sectional area of the hydrophilic region.

3. A linker lipid as claimed in claim 1 in which the attachment group has a cross sectional area greater than the cross sectional area of the hydrophobic region.

4. A linker lipid as claimed in claim 1 in which the hydrophilic region of the linker lipid is composed of oligo or poly ethers, oligo or poly peptides, oligo or poly amides, oligo or poly amines, oligo or poly esters, oligo or poly saccharides, polyols, multiple charged groups, electroactive species or combinations thereof.

5. A linker lipid as claimed in claim 1 in which the hydrophilic region consists of an oligoethylene oxide group.

6. A linker lipid as claimed in claim 5 in which the oligoethylene oxide group comprises four to twenty ethylene oxide units.

7. A linker lipid as claimed in claim 1 in which the hydrophilic region consists of a subunit of tetraethylene glycol attached to succinic acid.

8. A linker lipid as claimed in claim 7 in which the tetraethylene glycol/succinic acid subunit is repeated 1–4 times.

9. A linker lipid as claimed in claim 1 in which the hydrophilic region consists of mercaptoethanol, succinic acid, 1,4-diesterified 1,2,3,4-butanetetraol and succinic acid subunits.

10. A linker lipid as claimed in claim 9 in which the succinic acid/1,4-diesterified 1,2,3,4-butanetetraol is repeated 1–4 times.

11. A linker lipid as claimed in claim 1 in which the hydrophilic region consists of an oligopropylene glycol of between 1 to 20 propylene glycol units in length.

12. A linker lipid as claimed in claim 1 in which the hydrophilic region consists of oligopropylene glycols of between 2 and 8 propylene glycol units that are functionalized at each end with an N-alkyl imine functionality and that are joined together via acid units forming tertiary amides.

13. A linker lipid as claimed in claim 1 in which the hydrophilic region consists of oligoethylene glycols of between 2 and 10 ethylene glycol units that are functionalized at each end with an N-alkyl imine functionality and that are joined together via acid units forming tertiary amides.

14. A linker lipid as claimed in claim 1 in which the head group of the linker lipid comprises a receptor reactive with an analyte or a group which attaches to a protein receptor.

15. A linker lipid as claimed in claim 1 in which the head group of the linker lipid comprises a biotin or biotin derivative which complexes streptavidin, avidin or a biotin binding protein.

16. A linker lipid as claimed in claim 15 in which the biotin group is linked to the linker lipid via 1 to 8 aminocaproyl groups.

17. A linker lipid as claimed in claim 1 in which the hydrophobic region of the linker lipid comprises a hydrocarbon backbone of between 20–60 angstroms in length with sites of attachment at either end of the hydrocarbon backbone to which are attached at least two hydrocarbon side chains.

18. A linker lipid as claimed in claim 1 in which the hydrophobic region of the linker lipid comprises a hydrocarbon backbone of between 20–60 angstroms in length with sites of attachment at either end of the hydrocarbon backbone to which are attached at one end zero or one hydrocarbon sidechain and at least two to four hydrocarbon sidechains at the other end.

19. A linker lipid as claimed in claim 17 in which the hydrocarbon chains are attached to the hydrocarbon backbone via a polyhydroxylated hydrocarbon containing from 3 to 20 hydroxyl groups.

20. A linker lipid as claimed in claim 17 in which hydrocarbon chains are attached to the hydrocarbon backbone via glycerol, glutamic acid, erythritol, threitol or pentaerythritol groups.

21. A linker lipid as claimed in claim 17 in which the length of the hydrocarbon sidechains are approximately half the total length of the hydrocarbon backbone.

22. A linker lipid as claimed in claim 21 in which the hydrocarbon sidechains are phytanyl chains.

23. A linker lipid as claimed in claim 17 in which the hydrocarbon side chains are mono- or per-methylated hydrocarbon chains or a hydrocarbon chain unsubstituted or substituted with additional groups selected from alkyl, aryl, ether and amine groups.

24. A linker lipid as claimed in claim 1 in which the cross sectional area of the hydrophobic region is essentially the same as the cross sectional area of the attachment group.

25. A linker lipid as claimed in claim 1 in which the attachment group includes between one to three disulfide groups.

26. A linker lipid as claimed in claim 1 in which the attachment group includes up to 6 thiol groups.

27. A linker lipid as claimed in claim 1 in which the attachment group is thiooctic acid or bis-thiooctic acid derivative.

28. A linker lipid as claimed in claim 1 in which the attachment group is a cyclic oxidised form of dithiothreitol.

29. A linker lipid as claimed in claim 1 in which the attachment group contains one to three bis(4-hydroxymethyl)-1,2-dithiacyclopentane groups.

30. A linker lipid as claimed in claim 1 in which the attachment group contains a bis(4-hydroxymethyl)-1,2-dithiacyclopentane group where the hydrophilic region is attached via a 4-hydroxymethyl moiety of the bis(4-hydroxymethyl)-1,2-dithiacyclopentane and where the another 1-hydroxymethyl moiety is a hydroxy functionality or is further functionalized to a methyl ether, ethyl ether, propyl ether, acetate, or succinate, or a group of the formula $(CH_2)_nCOZ$ where n is 0 to 4, and Z is OR, or $NR^1R^2$, where R, $R^1$ and $R^2$ are independently hydrogen or alkyl chains containing between 1 and 4 carbon atoms.

31. A linker lipid as claimed in claim 1 in which the attachment group contains a bis(4-hydroxymethyl)-1,2-dithiacyclopentane group where the hydrophilic region is attached via a 4-hydroxymethyl moiety of the bis(4-hydroxymethyl)-1,2-dithiacyclopentane and where another 4-hydroxymethyl moiety is linked to between one and three other bis(4-hydroxymethyl)-1,2-dithiacyclopentane groups.

32. A linker lipid as claimed in claim 1 in which the attachment group contains one to three dithiothreitol groups.

33. A linker lipid as claimed in claim 1 in which the attachment group contains a trans-4,5-dihydroxy-1,2-dithiacyclohexane group where the hydrophilic region is attached via a 4,5-hydroxy moiety of the trans-4,5-dihydroxy-1,2-dithiacyclohexane and where another 4,5-hydroxy moiety is a hydroxy functionality or is further functionalized to a methyl ether, ethyl ether, propyl ether, acetate, or succinate, or a group of the formula $(CH_2)_nCOZ$ where n is 0 to 4, and Z is OR, or $NR^1R^2$, where R, $R^1$ and $R^2$ are independently hydrogen or alkyl chains containing between 1 and 4 carbon atoms.

34. A linker lipid as claimed in claim 1 in which the attachment group contains a trans-4,5-dihydroxy-1,2-dithiacyclohexane group where the hydrophilic region is attached via a 4,5-hydroxy moieties of the trans-4,5-dihydroxy-1,2-dithiacyclohexane and where another 4,5-hydroxy moiety is linked to between one and three other trans-4,5-dihydroxy-1,2-dithiacyclohexane groups.

35. A linker lipid as claimed in claim 1 in which an ionophore is covalently attached to the hydrophobic region of the linker lipid via at least one tethering chain which is long enough for the attached ionophore to traverse the membrane and transport ions across the membrane.

36. A linker lipid as claimed in claim 1 in which the attachment group has a cross sectional area at least 2 times the cross sectional area of the hydrophilic region.

37. A linker lipid as claimed in claim 17 in which the hydrocarbon side chains are phytanyl chains.

38. A linker lipid as claimed in claim 4 in which the multiple charged groups are positively and/or negatively charged.

39. A linker lipid for use in attaching a membrane including a plurality of ionophores to an electrode and providing a space between the membrane and the electrode in which the membrane is either in part or totally made up of the linker lipid, the linker lipid comprising within the same molecule a hydrophobic region spanning the membrane, an attachment group used to attach the molecule to an electrode surface, a hydrophilic region intermediate said hydrophobic region and the attachment group, and a polar head group region attached to the hydrophobic region at a site remote from the hydrophilic region wherein said attachment group has a cross sectional area greater than the cross sectional area of the hydrophilic region, in which the attachment group has the following structure:

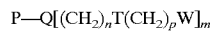

where P is either a carbon, nitrogen or oxygen to which the hydrophilic region is attached, Q is a carbon or if P is a carbon Q is a nitrogen, n is between 1 to 6, m is between 1 to 3 if Q is a carbon and between 1 to 2 if Q is a nitrogen, T is O, NH, $NR^1$, an amide or ketone, and where n is between 1 and 5 and p is between 2 and 5, unless Q is N, in which case n is between 2 and 5, and where $R^1$ is an alkyl chain containing between 1 and 4 carbon atoms, and W is a group of the formula:

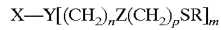

where X is either a carbon, nitrogen or oxygen, Y is a carbon or an alkyl chain of 1–4 carbons or if X is a carbon Y is a nitrogen, m is between 1 to 3 if Y is a carbon and between 1 to 2 if Y is a nitrogen, where Z is a bond, O, NH, $NR^1$, an amide or ketone, and where n is between 1 and 5 and p is between 2 and 5, unless Y is N, in which case n is between 2 and 5, and where $R^1$ is an alkyl chain containing between 1 and 4 carbon atoms, and R is —SH, —$SCH_2Ph$, —$SCH_2CO_2H$, —$SCH_2CH_2CO_2H$, —$SCH_2CH_2OH$, —$SCH_2CH_2CH_2OH$, —$SCH_3$, —$SCH_3$, $CH_3$, —$SCH_2CH_2CH_3$, —$SCH_2CO_2CH_3$, —$SCH_2CO_2CH_2CH_3$, an alkyl chain containing between 1 and 4 carbon atoms, or an aryl group.

* * * * *